US006130042A

United States Patent [19]
Diehl et al.

[11] Patent Number: 6,130,042
[45] Date of Patent: Oct. 10, 2000

[54] COMPOSITIONS AND METHODS FOR DIAGNOSING PERIODONTAL DISEASE

[75] Inventors: Scott R. Diehl, Gaithersburg, Md.; Harvey A. Schenkein, Richmond, Va.; Yue-Fen Wang, North Potomac, Md.

[73] Assignee: The United States of America as represented by the Department of Health and Human Services, Washington, D.C.

[21] Appl. No.: 09/035,220

[22] Filed: Mar. 5, 1998

[51] Int. Cl.[7] .............................. C12Q 1/68; C07H 21/04; C12P 19/34

[52] U.S. Cl. ......................... 435/6; 435/91.2; 435/91.52; 435/7.1

[58] Field of Search .......................... 435/6, 91.2, 91.52, 435/7.1

[56] References Cited

U.S. PATENT DOCUMENTS

| | | | |
|---|---|---|---|
| 4,683,195 | 7/1987 | Mullis et al. | 435/6 |
| 5,284,940 | 2/1994 | Lin et al. | 536/25.4 |
| 5,683,202 | 11/1997 | Hummel et al. | 403/325 |
| 5,686,246 | 11/1997 | Kornman et al. | 435/6 |

OTHER PUBLICATIONS diGiovine et al. Cytokine. 7: 606, Abstract A65, Aug. 1995.
Mansfield et al. Gastroenterology. 106:637–642, 1994.
Beck et al., "Periodontal Disease and Cardiovascular Disease," *J. Periodontol.*, 67: 1123–1127 (1996).
Bell et al., "Polymorphic DNA region adjacent to the 5' end of the human insulin gene," *Proc. Natl. Acad. Sci. USA* 78: 5759–5763 (1981).
Doty et al., "Strand Separation and Specific Recombination in Deoxyribonucleic Acids: Physical Chemical Studies," *Proc. Natl. Acad. Sci. USA* 46: 461–476 (1960).
Erlich (ed.), *PCR Technology*, p. 33, Stockton Press (1989).
Hart, "Genetic Risk Factors for Early–Onset Periodontitis," *J. Periodontol.*, 67: 355–366 (1996).
Kornman et al., "The interleukin–1 genotype as a severity factor in adult periodontal disease," *J. Clin. Periodontol.*, 24: 72–77 (1997.
Marmur and Lane, "Strand Separation and Specific Recombination in Deoxyribonucleic Acids: Biological Studies," *Proc. Natl. Acad. Sci. USA* 46: 453–461 (1960).
Nickerson et al., "Automated DNA diagnostics using an ELISA–based oligonucleotide ligation assay," *Proc. Natl. Acad. Sci. USA* 87: 8923–8927 (1990).
Offenbacher et al., "Periodontal Infection as a Possible Risk Factor for Preterm Low Birth Weight," *J. Periodontol.* 67: 1103–1113 (1996).
Schenkein, "Genetics of Early–Onset Periodontal Diseases," In *Molecular Pathogenesis of Periodontal Disease*, Genco (ed.), pp. 373–386, Am. Soc. Microbiol. (1994).
Studencki and Wallace, "Allele–Specific Hybridization Using Oligonucleotide Probes of Very High Specific Activity: Discrimination of the Human $\beta^A$– and $\beta^S$–Globin Genes," *DNA* 3: 7–15 (1984).
Studencki et al., "Discrimination among the Human $\beta^A$, $\beta^S$, and $\beta^C$–Globin Genes Using Allele–Specific Oligonucleotide Hybridization Probes," *Am J. Hum. Genet.* 37: 42–51 (1985).
Wahl et al., "Molecular Hybridization of Immobilized Nucleic Acids: Theoretical Concepts and Practical Considerations," in *Meth. Enzymol.*, 152: 399–415 (1987).
Genco, "Periodontal Disease and Risk for Myocardial Infarction and Cardiovascular Disease," *CVR & R*, pp. 34–40 (Mar. 1998).
Wu et al., "Examination of the Relation between Periodontal Health Status and Cardiovascular Risk Factors: Serum Total and High Density Lipoprotein Cholesterol, C–reactive Protein, and Plasma Fibrinogen," *Am. J. Epidemiol.*, 151: 273–282 (2000).
Parkhill et al., "Interleukin–1 gene polymorphisms and early onset periodontitis," *J. Dent. Res.*, 79: 520 (2000).
Van Dyke et al., "Linkage Disequilibrium of IL–1β Genotype in African American LJP Patients," *J. Dent. Res.*, 78: 555 (1999).

*Primary Examiner*—Carla J. Myers
*Attorney, Agent, or Firm*—Medlen & Carroll, LLP

[57] ABSTRACT

Compositions and methods are described for diagnosing periodontal disease, and in particular, early-onset periodontal disease. Nucleic acid-based testing is described which permits the detection of a high risk haplotype.

40 Claims, 4 Drawing Sheets

COMPOSITIONS AND METHODS FOR DIAGNOSING PERIODONTAL DISEASE

This invention was made with government support under Projects P50DE10703 and Z01DE00622 of NIDR,NIH. The government has certain rights in the invention.

FIELD OF THE INVENTION

The present invention relates to compositions and methods for diagnosing periodontal disease, and in particular, early-onset periodontal disease.

BACKGROUND

The early-onset periodontal diseases (EOP), including clinical syndromes designated localized juvenile periodontitis (LJP), generalized juvenile periodontitis (GJP), and rapidly progressive periodontitis (RPP), are characterized by their age of onset, which is usually after puberty, and the unusually rapid progression of periodontal attachment loss in affected individuals. EOP is also sometime manifested before puberty, and it is then called pre-pubertal periodontitis (PPP). The localized (LJP) and generalized (GJP, RPP) forms of EOP aid are distinguished by the pattern of teeth affected by such attachment loss. Classically, LJP has been defined by attachment loss at first molar and incisor teeth, while GJP affects a large number of teeth not limited to first molars and incisors.

EOP occurs after puberty but before age 35 and often results in pronounced tooth loss before the age of 20 years. The most recent National Survey of the Oral Health of U.S. Children aged 5 to 17 conducted in 1986–86 included periodontal assessment of 11,007 adolescents aged 14 to 17 years old. Nationwide, approximately 0.53% of these adolescents were estimated to have LJP, 0.13% had G-EOP, and 1.61% had incidental loss of attachment. If one projected these frequencies to the total U.S. population, one would estimate that approximately 70,000 persons aged 14 to 17 years old had LJP at the time of the survey and an additional 17,000 members of this age group has the more destructive G-EOP. Since both of these forms of EOP can also develop well after age 17 (by definition, up to age 35) the total number of EOP cases in the U.S. may be 2- to 4-fold higher than these numbers that are limited to the four year age range of the adolescent group. This means that from approximately 175,000 up to 350,000 EOP cases may exist in the U.S. population among the total adolescent and young adult population (age 14–35).

Recent studies have underscored the association of periodontal infections with certain medically important conditions. There are increasing data accumulating that implicate periodontal disease as a risk factor for cardiovascular diseases such as heart attack and stroke. See e.g. J. Beck et al., "Periodontal Disease and Cardiovascular Disease," *J. Periodontol.* 67:1123 (1996). Epidemiologic studies indicate that, even after accounting for other known risk factors for cardiovascular disease, the relative risk attributable to periodontal infections is significant. Secondly, recent studies have shown that mothers with periodontitis are at greater risk for having low weight babies than those without periodontitis. See Offenbacher et al., "Periodontal Infection as a Possible Risk Factor for Preterm Low Birth Weight," *J. Periodontol.* 67:1103 (1996).

Once symptoms are detected, treatment is difficult and expensive. It is believed that treatment results would be much better if individuals could be determined to be at risk prior to symptoms. In this manner, preventative measures could be taken and early intervention strategies could be employed. Unfortunately, determining concrete risk factors has been problematic.

Bacteria are recognized as the primary etiologic agents in periodontitis. Moreover, it is generally agreed that *Actinobacillus actinomycetemcomitans* is involved in the disease. However, microbial virulence appears to differ from person to person. Consequently, to date, no direct cause and effect relationship exists between any specific bacteria and type of periodontitis. As a result, the presence of a specific bacteria is not pathognomonic for any form of periodontitis. See T. A. Hart, "Genetic Risk Factors for Early-Onset Periodontitis," *J Periodontol.* 67:355 (1996).

Several putative genetic risk factors have been suggested for EOP, most of which are based upon data implicating aberrant host immunity or inflammatory reactions as likely pathogenic mechanisms. These factors include HLA antigens, factors related to aberrant polymorphonuclear leukocyte chemotactic function, and elevated or depressed cytokine and prostanoid production. See generally, H. A. Schenkein, "Genetics of Early-Onset Periodontal Diseases," In: *Molecular Pathogenesis of Periodontal Disease* (1994 ASM, Robert Genco, Ed.).

In all of the above-mentioned cases, it is hypothesized that the host response to bacterial etiologic agents is aberrant or deficient, resulting in expression of periodontitis at a young age. This hypothesis is supported by the observation that a number of defined genetic abnormalities associated with depressed phagocytic function predispose patients to periodontitis during early childhood. However, none of these risk factor studies have been consistently replicated, and most are based on small sample sizes and provide only weak statistical support for associations.

The actual genetic architecture of EOP susceptibility remains undetermined to date. What is needed is a reliable diagnostic based on genetic factors which identifies individuals at risk for EOP prior to the onset of symptoms. This would permit early monitoring and therapeutic intervention.

SUMMARY OF THE INVENTION

The present invention relates to compositions and methods for diagnosing periodontal disease, and in particular, early-onset periodontal disease. The present invention contemplates identifying risk for periodontal disease by detecting genes demonstrated herein to be associated with periodontal disease. The invention involves detection of genetic polymorphisms at the interleukin $1\alpha$ and $1\beta$ genes. There are two alleles for each of these genes (1A and 2A; 1B and 2B) which are defined by at least one base change.

The present invention contemplates testing to determine the genotype of a child or young adult to identify individuals at risk for disease. High risk genotypes are those where the individual is homozygous for allele 1 for IL-1B or homozygous for allele 1 for IL-1A, and the highest risk is presented where the individual is homozygous for allele 1 for IL-1B as well as being homozygous for allele 1 for IL-1A. The identification of a high risk genotype permits prospective testing on patients without symptoms (as well as patients with symptoms which cause one to suspect the disease is present).

In one embodiment, the present invention contemplates a method comprising a) providing i) a human sample (e.g. from a child or young adult) comprising nucleic acid, said nucleic acid comprising the IL-1B gene, and ii) a treatment means; and b) treating said sample with said treatment means under conditions such that a high risk genotype comprising a genotype homozygous for allele 1 at the IL-1B locus, if present, is detected. The method can further comprise the step (c) of treating said human having said homozygous genotype with antibacterial therapy.

In another embodiment, the present invention contemplates a method comprising a) providing i) a human sample (e.g. from a child or young adult) comprising nucleic acid, said nucleic acid comprising the IL-1A gene, and ii) a treatment means; and b) treating said sample with said treatment means under conditions such that a high risk genotype comprising a genotype homozygous for allele 1 at the IL-1A locus, if present, is detected. The method can further comprise the step (c) of treating said human having said homozygous genotype with antibacterial therapy.

It is not intended that the present invention be limited by the nature of the treatment means. In one embodiment, the treatment means comprises a restriction enzyme. In another embodiment, the treatment means comprises one or more labelled oligonucleotides (e.g. oligonucleotides capable of detecting the polymorphisms that define the various alleles).

In a preferred embodiment, the nucleic acid of said sample is amplified prior to said treating of step b). Indeed, said nucleic acid of said sample is amplified (e.g. by PCR) with primers capable of amplifying the IL-1A gene and (in a separate reaction) capable of amplifying the IL-1B gene. In this embodiment, the present invention contemplates a method, comprising: a) providing i) a human sample comprising nucleic acid, said nucleic acid comprising IL-1A and IL-1B genes, ii) first and second reaction means, iii) first and second oligonucleotide primers capable of amplifying a region of said IL-1A gene, and iv) third and fourth oligonucleotide primers capable of amplifying a region of said IL-1B gene; b) reacting said first and second oligonucleotide primers with a first portion of said sample in said first reaction means under conditions such that a first amplification product of the IL-1A gene is produced; c) reacting said third and fourth oligonucleotide primers with a second portion of said sample in said second reaction means under conditions such that a second amplification product of the IL-1B gene is produced; and d) treating said first and second amplification products under conditions such that a high risk genotype comprising a genotype homozygous for allele 1 at the IL-1B locus and/or homozygous for allele 1 at the IL-1A locus, if present, is detected.

In one embodiment, said treating at step (d) comprises digesting said first and second amplification products with one or more restriction enzymes. In another embodiment, said treating at step (d) comprises hybridizing a first pair of allele-specific oligonucleotide probes with said first amplification product and a second pair of allele-specific oligonucleotide probes with said second amplification product. In yet another embodiment, said treating at step (d) comprises hybridizing first, second and third ligation oligonucleotides (two of which allele-specific) to said first amplification product and third, fourth and fifth ligation oligonucleotides (two of which are allele-specific) to said second amplification product.

It is not intended that the present invention be limited by the nature of the target nucleic acid. The target nucleic acid may be a purified or non-purified. The target nucleic acid may be labelled or unlabelled. The target nucleic acid may be single- or double-stranded; however, it is contemplated that, if double-stranded, the nucleic acid will be rendered single-stranded for amplification.

In one embodiment, the sample is obtained from blood or tissue samples. In a preferred embodiment, the DNA is obtained from blood cells (e.g. lymphocytes) obtained from a finger prick of the patient with the blood collected on absorbent paper. The DNA is then isolated from the dried blood spots and then target sequences amplified using the polymerase chain reaction (PCR). Oligonucleotide DNA primers that target the specific polymorphic DNA region within the genes of interest are prepared so that in the PCR reaction amplification of the target sequences is achieved. This embodiment has the advantage of requiring only a small amount of blood and avoids the necessity for venipuncture or a tissue biopsy. The amplified DNA sequences from the template DNA are then analyzed using restriction enzymes to determine the genetic polymorphisms present in the amplified sequences and thereby provide a genetic polymorphism profile of the patient.

In yet another embodiment, the present invention contemplates a method of predicting a patient's susceptibility to increased periodontal disease severity, comprising the steps of a) isolating nucleic acid (e.g. genomic DNA) from a patient; b) determining a genetic polymorphism pattern for IL-1A and IL-1B in the genomic DNA so as to detect, if present, a high risk genotype comprising a genotype homozygous for allele 1 of IL-1B and/or homozygous for allele 1 of IL-1A. In one embodiment, the genetic polymorphism patterns of the sample are compared to a control sample (a sample of known genotype).

It is not intended that the present invention be limited to the race of the human tested (or ethnic group or geographical origin). While the study described below involves the testing of African-Americans and Caucasians, these findings can be readily extended to other groups. In this regard, where another group has a higher frequency of the 2 allele for either or both IL-1A and IL-1B, it is expected that individuals in this group having the 1 allele (even those who are heterozygous for the 1 and 2 alleles) will show a higher risk than those individuals who are homozygous for the 2 allele.

Definitions

To facilitate understanding of the invention, a number of terms are defined below.

"Initiating a reaction" means causing a reaction to take place. Reactions can be initiated by any means (e.g. heat, wavelengths of light, addition of a catalyst, etc.)

"Reaction means" is any means for carrying out a reaction, including containers of all sorts (e.g. tubes) as well as reaction wells, channels and chambers (including but not limited to microwells, microchannels and microchambers). "Reaction means" can also be solid supports such as beads, gels and surfaces (e.g. filter paper, nitrocellulose, etc.).

A "treatment means" is any means capable of revealing a high risk genotype, including but not limited to restriction enzymes and oligonucleotide primers and probes.

The term "gene" refers to a DNA sequence that comprises control and coding sequences necessary for the production of a polypeptide or precursor thereof. The polypeptide can be encoded by a full length coding sequence or by any portion of the coding sequence so long as the desired enzymatic activity is retained.

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "oligonucleotide" as used herein is defined as a molecule comprised of two or more deoxyribonucleotides or ribonucleotides, usually more than three (3), and typically more than ten (10) and up to one hundred (100) or more (although preferably between twenty and thirty). The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, oligonucleotides anneal to complementary strands of nucleic acid:

5'-ATTC . . . -3' (primer A)
5'-ATTC . . . GCCA-3'
3'-TAAG . . . CGGT-5'
   3'-CGGT-5' (primer B)

it is customary that one primer (primer A) be called the "upstream" primer and the other (primer B) the "downstream" primer.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

"Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, *Proc. Natl. Acad. Sci. USA* 46:453 (1960) and Doty et al., *Proc. Natl. Acad. Sci. USA* 46:461 (1960) have been followed by the refinement of this process into an essential tool of modem biology. Nonetheless, a number of problems have prevented the wide scale use of hybridization as a tool in human diagnostics. Among the more formidable problems are: 1) the inefficiency of hybridization; 2) the low concentration of specific target sequences in a mixture of genomic DNA; and 3) the hybridization of only partially complementary probes and targets.

With regard to efficiency, it is experimentally observed that only a fraction of the possible number of probe-target complexes are formed in a hybridization reaction. This is particularly true with short oligonucleotide probes (less than 100 bases in length). There are three fundamental causes: a) hybridization cannot occur because of secondary and tertiary structure interactions; b) strands of DNA containing the target sequence have rehybridized (reannealed) to their complementary strand; and c) some target molecules are prevented from hybridization when they are used in hybridization formats that immobilize the target nucleic acids to a solid surface.

Even where the sequence of a probe is completely complementary to the sequence of the target, i.e., the target's primary structure, the target sequence must be made accessible to the probe via rearrangements of higher-order structure. These higher-order structural rearrangements may concern either the secondary structure or tertiary structure of the molecule. Secondary structure is determined by intramolecular bonding. In the case of DNA or RNA targets this consists of hybridization within a single, continuous strand of bases (as opposed to hybridization between two different strands). Depending on the extent and position of intramolecular bonding, the probe can be displaced from the target sequence preventing hybridization.

Solution hybridization of oligonucleotide probes to denatured double-stranded DNA is further complicated by the fact that the longer complementary target strands can renature or reanneal. Again, hybridized probe is displaced by this process. This results in a low yield of hybridization (low "coverage") relative to the starting concentrations of probe and target.

With regard to low target sequence concentration, the DNA fragment containing the target sequence is usually in relatively low abundance in genomic DNA. This presents great technical difficulties; most conventional methods that use oligonucleotide probes lack the sensitivity necessary to detect hybridization at such low levels.

One attempt at a solution to the target sequence concentration problem contemplated by the present invention is the amplification of the detection signal. Most often this entails placing one or more labels on an oligonucleotide probe. In the case of radioactive oligonucleotide probes, only extremely high specific activities are found to show satisfactory results. See Studencki and Wallace, DNA 3:1 (1984) and Studencki et al., Human Genetics 37:42 (1985).

K. B. Mullis et al., U.S. Pat. Nos. 4,683,195 and 4,683,202, hereby incorporated by reference, describe a method for increasing the concentration of a segment of a target sequence in a mixture of genomic DNA without cloning or purification. This process for amplifying the target sequence (which can be used in conjunction with the present invention to make target molecules) consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then to annealed to their complementary sequences within the target molecule. Following annealing, the primers are extended with a polymerase so as to form a new pair of complementary strands. The steps of denaturation, primer annealing, and polymerase extension can be repeated many times (i.e. denaturation, annealing and extension constitute one "cycle;" there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to by the inventors as the "Polymerase Chain Reaction" (hereinafter PCR). Because the desired amplified segments of the target sequence become the predominant sequences (in terms of concentration) in the mixture, they are said to be "PCR amplified". The result of the cycling is also referred to as an "amplification product."

With PCR, it is possible to amplify a single copy of a specific target sequence in genomic DNA to a level detectable by several different methodologies (e.g. hybridization with a labelled probe; incorporation of biotinylated primers followed by avidin-enzyme conjugate detection; incorporation of $^{32}$P labelled deoxynucleotide triphosphates, e.g. dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

The PCR amplification process is known to reach a plateau concentration of specific target sequences of approximately $10^8$ M. A typical reaction volume is 100 μl, which corresponds to a yield of $6 \times 10^{11}$ double stranded product molecules.

Hybridization, regardless of the method used, requires some degree of complementarity between the sequence being assayed (the target sequence) and the fragment of DNA used to perform the test (the probe). (Of course, one can obtain binding without any complementarity but this binding is nonspecific and to be avoided.)

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Stability of a nucleic acid duplex is measured by the melting temperature, or "$T_m$." The $T_m$ of a particular nucleic acid duplex under specified conditions is the temperature at which on average half of the base pairs have disassociated. The equation for calculating the $T_m$ of nucleic acids is well known in the art. As indicated by standard references, an estimate of the $T_m$ value may be calculated by the equation:

$$T_m = 81.5° C. + 16.6 \log M + 0.41(\%GC) - 0.61(\% \text{form}) - 500/L$$

where M is the molarity of monovalent cations, %GC is the percentage of guanosine and cytosine nucleotides in the DNA, % form is the percentage of formamide in the hybridization solution, and L=length of the hybrid in base pairs [see e.g., Guide to Molecular Cloning Techniques, Ed. S. L. Berger and A. R. Kimmel, in Methods in Enzymology Vol. 152, 401 (1987)]. Other references include more sophisticated computations which take structural as well as sequence characteristics into account for the calculation of $T_m$.

The term "probe" as used herein refers to a labeled oligonucleotide which forms a duplex structure with a sequence in another nucleic acid, due to complementarity of at least one sequence in the probe with a sequence in the other nucleic acid.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like. Such labels can be added to the oligonucleotides of the present invention.

The terms "nucleic acid substrate" and nucleic acid template" are used herein interchangeably and refer to a nucleic acid molecule which may comprise single- or double-stranded DNA or RNA.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

The term "sequence variation" as used herein refers to differences in nucleic acid sequence between two nucleic acid templates. It is noted, however, that the invention does not require that a comparison be made between one or more forms of a gene to detect sequence variations.

The term "nucleotide analog" as used herein refers to modified or non-naturally occurring nucleotides such as 7-deaza purines (i.e., 7-deaza-dATP and 7-deaza-dGTP). Nucleotide analogs include base analogs and comprise modified forms of deoxyribonucleotides as well as ribonucleotides. As used herein the term "nucleotide analog" when used in reference to substrates present in a PCR mixture refers to the use of nucleotides other than dATP, dGTP, dCTP and dTTP; thus, the use of dUTP (a naturally occurring dNTP) in a PCR would comprise the use of a nucleotide analog in the PCR. A PCR product generated using dUTP, 7-deaza-dATP, 7-deaza-dGTP or any other nucleotide analog in the reaction mixture is said to contain nucleotide analogs.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRS, RT-PCRs and the like.

A "consensus gene sequence" refers to a gene sequence which is derived by comparison of two or more gene sequences and which describes the nucleotides most often present in a given segment of the genes; the consensus sequence is the canonical sequence.

The term "polymorphic locus" is a locus present in a population which shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

As used herein, "a child suspected to be at risk for early-onset periodontal disease" and "a young adult suspected to be at risk for early-onset periodontal disease" refers to a child (a person 19 years and under) or young adult (a person between 20 and 35 years of age) prior to testing for the IL1 genotypes who has one or more of the following indications or risk factors:
1. One or more parent, sibling, half-sibling, grandparent, aunt, uncle or cousin with a diagnosis of EOP.
2. A person with the above types of relatives with a history of periodontitis at a relatively young age (<40 years old), even if available data do not permit a definitive diagnosis of EOP.
3. A person with the above types of relatives with a history of tooth loss at a relatively young age (<40 years old), where other reasons for the tooth loss such as caries or strategic elective extractions are not a factor.
4. A person who is a moderate or heavy smoker.

DESCRIPTION OF THE INVENTION

Figure 1:
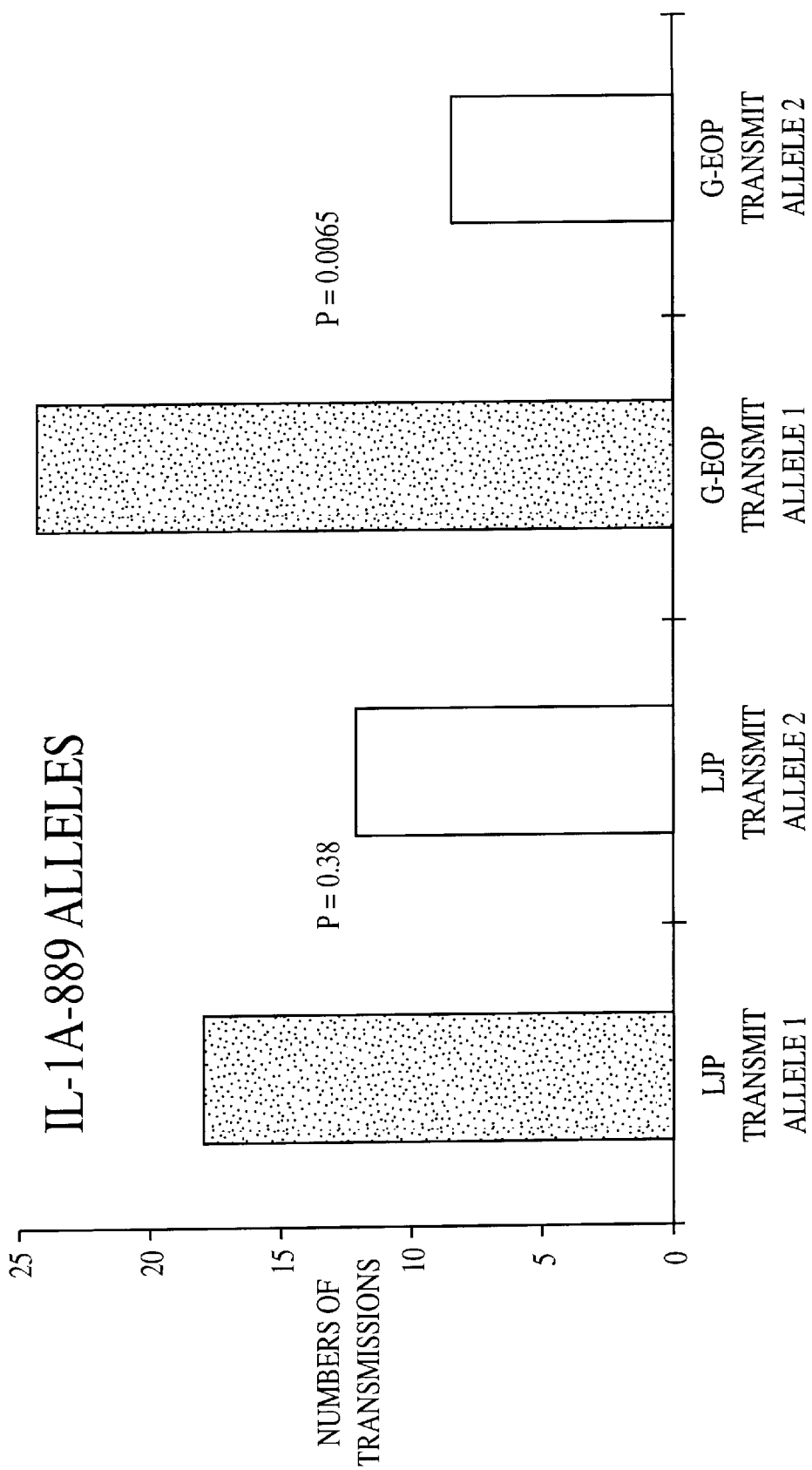
FIG. 1 is a graph showing that allele 1 of the IL-1A –889 marker is transmitted significantly more often than allele 2 to G-EOP affected individuals.

The present invention relates to compositions and methods for diagnosing periodontal disease, and in particular, early-onset periodontal disease. The present invention contemplates identifying risk for periodontal disease by detecting genes demonstrated herein to be associated with periodontal disease. The invention involves detection of genetic polymorphisms at the interleukin 1α and 1β genes.

A recent report by Kornman et al, *J. Clin. Periodontal.*, 24:72 (1997) suggested that genetic polymorphisms at the interleukin 1α and 1β genes may be associated with severity of periodontitis in adult non-smokers; it was reported that non-smokers aged 40–60 carrying the "2" allele (in either homozygous or heterozygous states) at both loci were observed to have nearly 19 times the risk of developing severe periodontitis compared to subjects homozygous for the "1" allele at either or both of these loci.

By contrast, the present invention contemplates testing which (by virtue of the correlation study herein described) are associated with high risk for periodontal disease. In particular, the present invention contemplates the identification of a high risk genotype comprising a genotype homozygous for allele 1 at the IL-1B locus and/or the IL-1A locus. The polymorphisms are discussed in more detail below. It is not intended that the present invention be limited to particular assay designs or formats. As discussed below, a variety of assay configurations and approaches are contemplated.

A. Assay Design

A common form of variation (polymorphism) among the DNA sequences of individual humans consists of substitutions of single nucleotides (e.g., T substituting for C, G for A, G substituting for A, C or T, etc.). Such Single Nucleotide Polymorphisms (commonly abbreviated "SNPs") may occur either within the coding portions of a gene, where they may change the amino acid composition of the protein transcribed and translated from the gene, or elsewhere, where they may influence the biological function of a nearby gene or genes by altering aspects of gene expression. Many different molecular methods have been developed for detection of DNA polymorphisms and are in routine use in genetics laboratories throughout the world for genetic diagnosis and other purposes.

One method contemplated by the present invention comprises combining DNA amplification by PCR followed by Restriction Fragment Length Polymorphism (RFLP) gel-based analyses (the combination of the two is abbreviated PCR/RFLP). Alternative methods include, but are not limited to:

1. RFLP analysis without prior PCR of the target fragment of interest. This older method, when properly applied, is equal in accuracy to the PCRIRFLP method, but requires larger quantities of human tissue (e.g., blood) than the PCR method and is usually more expensive and time-consuming to apply on a large scale.

2. The Oligonucleotide Ligation Assay (abbreviated OLA) combines a PCR amplification of the region of the genome surrounding the SNP, followed by a ligation reaction between alternative pairs of oligonucleotides that ligate together only if there is a perfect sequence match between the oligonucleotides and the DNA template derived from the subject's DNA. See D. A. Nickerson et al., "Automated DNA diagnostics using an ELISA-based oligonucleotide ligation assay," *Proc. Natl. Acad. Sci. USA* 87:8923 (1990). For common applications of this method three oligonucleotides are used (usually oligos that are approximately 18–24 bp in length). The task is to determine which of two alternative nucleotide bases is present in the DNA sequence as a specific position. One of the oligonucleotides is used in the detection of both of the alleles, and this is synthesized with biotin for later capture on strepavidin-coated microtitre plates. It is designed to match the DNA sequence directly adjacent to the polymorphic site. Each of the two oligonucleotides are identical in sequence to only one of the two alternative alleles being assayed, differing only at the polymorphic DNA site at their end next to the biotinylated oligonucleotide. These are each labeled with a different chemical (e.g., fluorescein, digoxygenein et al.) that can be distinguished by standard detection methods. If both copies (maternal and paternal) of the human subject's DNA surrounding the SNP (previously amplified by PCR) matches only one of the two variable oligonucleotides used in the ligation assay, then only that matching oligonucleotide will ligate with the adjacent biotin labeled oligonucleotide. The ligated combination of the biotinylated oligonucleotide and one of the labeled oligonucleotides is then captured in a strepavidin-coated microtitre plate, while the other oligonucleotide (matching the alternative polymorphic allele that was not present in the human subject's DNA sequence) does not ligate to the biotinylated oligonucleotide and so it is washed out of the microtitre plate well. After washing, standard detection assays are performed for both of the two oligonucleotides' labels; if only one of the alleles is present in the subject's DNA, then only one ligation product will be detected. Alternatively, if the individual is heterozygous, and contains a copy of one allele on the maternal chromosome and the other allele on the paternal chromosome, both of the labeled oligonucleotides will match the subject's PCR-amplified template DNA and, therefore, both will ligate successfully to the biotinylated oligonucleotide and be detected on the strepavidin-coated plate. The advantages of the method are that it is performed using standard microtitre plate labeling methods (and thus is highly efficient, easily automatable and potentially less costly than gel-based assays) and it is usually much more accurate than restriction based assays (which can be subject to false positives or false negatives due to problems of partial digestion).

3. The Dot Blot method is used to detect SNPs by first PCR amplifying human subject's genomic DNA for the region surrounding the SNP and then binding the amplified DNA to a nylon membrane and hybridizing it with oligonucleotides that match either of the two alternative genetic alleles of the SNP. Buffer and temperature conditions are adjusted (discussed more below as allele-specific hybridization) so that the labeled oligonucleotide will only remain hybridized to the membrane-bound DNA only if there is a perfect sequence match. The two different probe oligonucleotides can either be labeled with different chemicals (e.g., fluroescein or digoxygenin) and hybridized and detected at the same time. Alternately, one oligonucleotide can be used to probe the membrane, stripped off afterwards, then the membrane can be probed again with the other probe oligonucleotide labeled with the same chemical as the first probe. As with the OLA method, if the subject has inherited the same SNP allele being studied on both maternal and paternal chromosomes, then only one of the labeled oligonucleotides will hybridize to the subject's amplified DNA that is bound to the membrane. If the subject is heterozygous, both oligonucleotides will bind and be detected.

4. The Reverse Dot Blot method employs the same basic strategy as the Dot Blot method, except that the two probe oligonucleotides are bound to the membrane and the PCR-amplified human subject's DNA is hybridized and binds only to matching probe alleles.

B. Polymorphisms

1. IL-1A: (Chromosome 2 at 2q12-14)

The alleles of a bi-allelic polymorphism of a single base variation (C/T) are to be distinguished in one embodiment of the present invention. While the difference can be identified by allele-specific cleavage using a restriction enzyme, in a preferred embodiment, the present invention contemplates primers in a hybridization reaction that permits only complete complementarity, thereby distinguishing between the single base difference. In this regard, allele 1 is C and allele 2 is T as shown below, wherein a partial sequence (SEQ ID NO:1) of the IL-1.alpha gene (from GenBank Accession No.: X03833) is set forth and the polymorphic site is indicated by [T/C]):

451 TTCATTTGCT AAGAGTCTGG TGTTCTACCA CCTGAACTAG

491 GCTGGCCACA GGAATTATAA AAGCTGAGAA ATTCTTTAAT

531 AATAGTAACC AGGCAACA[T/C]C ATTGAAGGCT CATATGTAAA AATCCATGCC TTCCTTTCTC

The polymorphic site is located at base −889; since the GenBank sequence (Accession No.: X03833) indicates transcription begins at base 1438, this corresponds to base 549 for the GenBank sequence.

Where the polymorphism is to be identified by using a restriction enzyme, a full restriction enzyme recognition site can be created by introducing a mutation in the PCR reaction with a modified primer sequence. The site is completed by the sequence of one of the alleles of the polymorphism. After restriction enzyme digestion of the products of the PCR reaction, the DNA is separated electrophoretically by size. From this gel (or a southern blot of it probed with a radioactive internal DNA sequence) the alleles of the polymorphism are identified. More specifically, using a portion of SEQ ID NO: 1 from above (SEQ ID NO:2), showing a portion of the complementary strand (SEQ ID NO:3), and the primers (SEQ ID NOS:4 and 5) described by Kornman et al, *J. Clin. Periodontal.*, 24:72 (1997), one approach can be shown for introducing a restriction site (in this case the NcoI restriction site=CCATGG) through a mutation (X=C):

5'-AAGCTTGTTC TACCACCTGA ACTAGGC-3' (SEQ ID NO:4)

ACAAGATGGT GGACTTGATC CG (SEQ ID NO:3)

TGTTCTACCA CCTGAACTAG GCTGGCCACA GGAATTATAA AAGCTGAGAA ATTCCTTTAAT AAT-AGTAACC AGGCAACA[T/C]C ATTGAAGGCT CATATGTAA (SEQ ID NO:2)

Using this system, the uncut fragment (larger) contains the T (and is the rarer allele in Northern European populations) while the cut fragment contains the restriction sequence CCATGG.

The present invention also contemplates allele-specific hybridization in order to identify the different alleles. In this approach, oligos are used that are completely complementary to each of the alleles; such oligos can be used in a dot blot format (discussed above) after the region containing the polymorphism has been amplified with standard upstream and downstream primers in PCR. As is well-known with hybridization techniques, discrimination of complete or partial complementarity is largely a function of the temperature used for the reaction. Where complete complementarity is desired, a high stringency reaction can be achieved by using temperatures near, at or above the $T_m$ (i.e. a reaction at temperatures below the $T_m$ are usually a low stringency reaction which permits hybridization where there is only partial complementarity is present). As noted in the definition section above, $T_m$ is controlled in part by the G/C content of the nucleic acid forming the duplex and the length of the base pairing region. For allele-specific hybridization, oligonucleotides of between 8 and 40 bases in length, and more preferably, 10-mers to 30-mers, and still more preferably, 12-mers to 24-mers, can be used. The oligos can be labelled or unlabelled; in a dot blot format, it is convenient to use labelled probes. For enhanced discrimination, oligos can contain be used that permit covalent attachment as set forth in U.S. Pat. No. 5,652,096, hereby incorporated by reference.

Examples of illustrative probes for allele-specific hybridization are shown below. Of course, the optimal conditions for each probe can be determined empirically with a variety of buffers and temperatures to arrive at conditions that reliable produce allele-specific hybridization.

1. Oligos for Allele 1

3'-TCCGTTGTGGTAACTTCCGAGTATACATT-5' (SEQ ID NO:6)

3'-CCGTTGTGGTAACTTCCGAGTATACATT-5' (SEQ ID NO:7)

3'-CGTTGTGGTAACTTCCGAGTATACATT-5' (SEQ ID NO:8)

3'-GTTGTGGTAACTTCCGAGTATACATT-5' (SEQ ID NO:9)

3'-TTGTGGTAACTTCCGAGTATACATT-5' (SEQ ID NO:10)

3'-TGTGGTAACTTCCGAGTATACAT-5' (SEQ ID NO: 11)

3'-GTGGTAACTTCCGAGTATACA-5' (SEQ ID NO: 12)

3'-TGGTAACTTCCGAGTATA-5' (SEQ ID NO:13)

3'-GGTAACTTCCGAGTATACATT-5' (SEQ ID NO:14)

2. Oligos for Allele 2

3'-TCCGTTGTAGTAACTTCCGAGTATACATT-5' (SEQ ID NO:15)

3'-CCGTTGTAGTAACTTCCGAGTATACATT-5' (SEQ ID NO:16)
3'-CGTTGTAGTAACTTCCGAGTATACATT-5' (SEQ ID NO:17)
3'-GTTGTAGTAACTTCCGAGTATACATT-5' (SEQ ID NO:18)
3'-TTGTAGTAACTTCCGAGTATACATT-5' (SEQ ID NO:19)
3'-TGTAGTAACTTCCGAGTATACAT-5' (SEQ ID NO:20)
3'-GTAGTAACTTCCGAGTATACA-5' (SEQ ID NO:21)
3'-TAGTAACTTCCGAGTATA-5' (SEQ ID NO:22)
3'-AGTAACTTCCGAGTATACATT-5 (SEQ ID NO:23)

If PCR is desired, primers embodied by SEQ ID NOS: 14 and 23 are particularly useful as allele-specific primers because they terminate at their 3'-ends with the polymorphic site. Of course, for PCR, a second primer is needed; this can be readily designed from looking at the remainder of the sequence (i.e. using the GenBank sequence or the portion of the GenBank sequence shown above). For example, the oligos (e.g. SEQ ID NOS: 14 and 23) could be used together with the Kornman primer discussed above, or longer or shorter variations thereof such as:

5'-TGTTCTACCACCTGAACTAGGC-3) (SEQ ID NO:24).

The oligonucleotides embodied by SEQ ID NOS:14 and 23 can also be used in ligation reactions. Of course, the ligation reaction requires a second oligo which will hybridize to the same strand adjacent to the oligos which hybridize to the polymorphic region. Such oligos can be readily designed from the remainder of the gene sequence (shown above).

2. IL-1B: (Chromosome 2; 2q12-14)

A bi-allelic polymorphism is again to be distinguished. While this can be done using allele-specific cleavage at naturally-occurring sites in the alleles (to yield different products), the present invention also contemplates primers in a hybridization reaction that permits only complete complementarity, thereby distinguishing between the single base difference. Again, allele 1 is C and allele 2 is T; the single base variation (C/T) contemplated for testing according to the teachings of the present invention is +3953 (referred to as IL-1B (TaqI)). This polymorphic site is shown below, wherein a partial sequence (SEQ ID NO:25) of the IL-1.beta gene (from GenBank Accession No.: X04500) is set forth and the polymorphic site is indicated by [T/C]):

5761 GACTTTGACC GTATATGCTC AGGTGTCCTC CAAGAAATCA
5801 AATTTTGCCA CCTCGCCTCA CGAGGCCTGC CCTTCTGATT
5841 TTATACCTAA ACAACATGTG CTCCACATTT CAGAACCTAT
5881 CTTCTI[T/C]GAC ACATGGGATA ACGAGGCTTA TGTGCACGAT
5921 GCACCTGTAC GATCACTGAA CTGCACGCTC CGGGACTCAC
5961 AGCAAAAAAG CTTGGTGATG TCTGGTCCAT ATGAACTGAA

The polymorphic site is located at base +3953; since the GenBank sequence (Accession No.: X04500) indicates transcription begins at base 1934, this corresponds to base 5887 for this GenBank sequence (it should be noted that GenBank Accession No: M15840 lacks the G shown in bold above at position 5783). As shown above, the polymorphic site is within the recognition sequence (TCGA) for the restriction enzyme TaqI. Thus, the polymorphism can be identified by using a restriction enzyme after amplification (e.g. in PCR) with two primers that encompass the site.

However, for convenience (i.e. easy detection of different size fragments), another restriction enzyme recognition site (e.g. TaqI) can again be created by introducing a mutation in the PCR reaction with a modified primer sequence. More specifically, using SEQ ID NO:25, showing a portion of the complementary strand (SEQ ID NO:26), and the primers (SEQ ID NOS:27 and 28) described by Kornman et al, *J. Clin. Periodontal.*, 24:72 (1997), one approach can be shown for introducing the restriction site through a mutation (X=G):

5'-CTC AGGTGTCCTC XAAGAAATCAAA-3' (SEQ ID NO:27)
GAG TCCACAGGAG GTTCTTTAGTT (SEQ ID NO:26)
5761 GACTTTGACC GTATATGCTC AGGTGTCCTC CAAGAAATCAAA
5803 TTTTGCCA CCTCGCCTCA CGAGGCCTGC CCTTCTGATT
5841 TTATACCTAA ACAACATGTG CTCCACATTT CAGAACCTAT
5881 CTTCTI[T/C]GAC ACATGGGATA ACGAGGCTTA TGTGCACGAT
5921 GCACCTGTAC GATCACTGAA CTGCACGCTC
5951 CGGGACTCAC AGCAAAAAAG CTTGGTGATG TCTGGTCCAT ATGAACTGAA (SEQ ID NO:25)
3'-CCCTGAGTG TCGTTTTTTC G-5' (SEQ ID NO:28)

Using this system, the PCR product containing the T in the polymorphic site will contain only one restriction sequence, while the PCR product fragment containing the C in the polymorphic site will contain two restriction sequences.

As noted above, however, the present invention contemplates allele-specific hybridization in order to identify the different alleles. In this approach, oligos are used that are completely complementary to each of the alleles. Again, it is not intended that the present invention be limited to particular oligos of particular length.

Examples of illustrative probes for allele-specific hybridization (e.g. for use in a dot blot format) are shown below. Again, the optimal conditions for each probe can be determined empirically with a variety of buffers and temperatures to arrive at conditions that reliably produce allele-specific hybridization.

1. Oligos for Allele 1
3'-GAAGAAGCTG TGTACCCTAT TGCTCCGAA-5 (SEQ ID NO:29)
3'-GAAGAAGCTG TGTACCCTAT TGCTCCGA-5 (SEQ ID NO:30)
3'-GAAGAAGCTG TGTACCCTAT TGCTCCG-5 (SEQ ID NO:31)
3'-GAAGAAGCTG TGTACCCTAT TGCTCC-5 (SEQ ID NO:32)
3'-AAGAAGCTG TGTACCCTAT TGCTC-5 (SEQ ID NO:33)
3'-AGAAGCTG TGTACCCTAT TGCT-5 (SEQ ID NO:34)
3'-GAAGCTG TGTACCCTAT TGC-5 (SEQ ID NO:35)
3'-AAGCTG TGTACCCTAT TG-5 (SEQ ID NO:36)
3'-GCTG TGTACCCTAT TGCTCCGAA-5 (SEQ ID NO:37)

2. Oligos for Allele 2
3'-GAAGAAACTG TGTACCCTAT TGCTCCGAA-5' (SEQ ID NO: 38)
3'-GAAGAAACTG TGTACCCTAT TGCTCCGA-5' (SEQ ID NO: 39)
3'-GAAGAAACTG TGTACCCTAT TGCTCCG-5' (SEQ ID NO: 40)
3'-GAAGAAACTG TGTACCCTAT TGCTCC-5' (SEQ ID NO: 41)
3'-AAGAAACTG TGTACCCTAT TGCTC-5' (SEQ ID NO: 42)
3'-AGAAACTG TGTACCCTAT TGCT-5' (SEQ ID NO: 43)

3'-GAAACTG TGTACCCTAT TGC-5' (SEQ ID NO: 44)
3'-AAACTG TGTACCCTAT TG-5' (SEQ ID NO: 45)
3'-ACTG TGTACCCTAT TGCTCCGAA-5 (SEQ ID NO:46)

If PCR is desired, primers embodied by SEQ ID NOS: 37 and 46 are particularly useful as allele-specific primers because they terminate at their 3'-ends with the polymorphic site. Of course, for PCR, a second primer is needed; this can be readily designed from looking at the remainder of the sequence (i.e. using the GenBank sequence or the portion of the GenBank sequence shown above). For example, the oligos (e.g. SEQ ID NOS: 37 and 46) could be used together with the Kornman primer for IL1-B discussed above (SEQ ID NO:27), or longer or shorter variations thereof such as: (SEQ ID NO:47) 5'-AGGTGTCCTCCAAGAAATCA-3'

The oligonucleotides embodied by SEQ ID NOS:37 and 46 can also be used in ligation reactions. Of course, the ligation reaction requires a second oligo which will hybridize to the same strand adjacent to the oligos which hybridize to the polymorphic region. Such oligos can be readily designed from the remainder of the gene sequence (shown above).

C. Sources of Nucleic Acid

As noted above, it is not intended that the present invention be limited by the nature of the target nucleic acid, the nucleic acid probed for the specific allelic sequence. The target nucleic acid may be a purified or non-purified. The target nucleic acid may be single- or double-stranded; however, it is contemplated that, if double-stranded, the nucleic acid will be rendered single-stranded prior to hybridization with the specific oligonucleotide(s).

It is not intended, moreover, that the present invention be limited to particular sources or types of samples. In one embodiment, whole blood is contemplated as a source of nucleic acid. Almost one half the volume of whole blood is occupied by cells, which consist largely of red blood cells (normal range: $4.2-6.1 \times 10^6$/ul), much smaller numbers of white blood cells (normal range: $1.0-10.8 \times 10^3$/ul) and platelets (normal range: $130-400 \times 10^3$/ul). The liquid portion, the blood plasma, is 90% water. The major plasma constituents include plasma proteins, organic metabolites and waste products, and inorganic components. Any one of these constituents may create difficulties with nucleic acid assays.

One class of constituents known to inhibit nucleic acid associated enzymes are the "hemes" which include hemin and hematin. Hemin has been reported to inhibit reverse transcriptase (RTase), DNA ligase, cytoplasmic DNA polymerase, and Taq polymerase. Since the present invention contemplates using PCR (as well as other techniques), inhibition of this amplification procedure is to be avoided. Hematin is inhibitory to PCR at a final concentration of 0.8 $\mu$M or higher (PCR Technology, H. A. Erlich (ed.) Stockton Press (1989) p. 33). "Protoporphyrin" is inhibitory at 20 $\mu$M. Non-heme blood components such as globin, Fe++ and Fe$^{+++}$ ions also inhibit PCR. One approach to overcoming the inhibition is to add more reagent and "swamp" the inhibition. This has been attempted in the case of PCR inhibition. It has been shown that, while hematin inhibition cannot be overcome by additional quantities of template DNA, it can be overcome by additional quantities of Taq polymerase or primer.

This swamping approach has a serious disadvantage: additional quantities of reagents may cause spurious results. Indeed, in the case of PCR it is known that additional quantities of Taq polymerase or primers can result in non-specific amplification products.

Another approach to avoid inhibition is to manipulate whole blood so as to isolate lymphocytes. This typically involves the isolation of white blood cells by centrifugation through a Ficoll gradient. The red blood cells and granulocytes pellet in this system. The lymphocyte-enriched white blood cells are recovered from the gradient interface. To remove Ficoll, which inhibits Taq polymerase, the cells are usually washed one or more times by centrifuging and removing the supernatant. Although this procedure yields lymphocytes free of red blood cells and most of the platelets, there are a number of disadvantages to this procedure, including: (1) relatively large, freshly drawn blood samples must be layered over Ficoll carefully so that the interface is undisturbed; (2) lymphocytes must be collected (after centrifugation) by removing the opaque band of cells located at the gradient interface and, (3) the collected lymphocytes must be washed free of Ficoll. The careful layering of blood is a slow and somewhat artful step. The collection of the cells at the gradient interface demands that i) enough blood be used initially such that the cells can be seen with the naked eye, ii) the cells be captured in a pipette (a cumbersome and low-yield technique), and iii) amplification be carried out in a different reaction vessel from that used to layer the blood. Finally, the approach utilizes a polymerase inhibitor (i.e. Ficoll) in large amounts that is not easily removed except by centrifugation. These drawbacks have seriously hindered the application of amplification techniques to large-scale clinical diagnostics.

A preferred approach to the inhibition is to treat blood to inactivate the polymerase inhibitors. Such an approach is set forth in U.S. Pat. No. 5,284,940, hereby incorporated by reference.

Of course, sources other than blood are contemplated, such as tissue sources (e.g. cells obtained from oral rinses or buccal brushing, skin and other organs). Buccal brushing, which will yield epithelial cells, is a convenient and minimally invasive procedure and therefore is preferred.

D. Kits and Components

As should now be clear from the above, the present invention provides compositions and methods for diagnosing periodontal disease, and in particular, early-onset periodontal disease. The compositions, such as oligonucleotides (useful as probes and/or primers), may be supplied in kit form. Additional elements of the kit include, but are not limited to, nucleic acid collection means and/or purification means, buffers, diluents, and controls.

E. Additional Testing

The present invention contemplates combining the power of the above-described genetic testing for polymorphisms at the interleukin 1$\alpha$ and 1$\beta$ genes with tests for other risk factors. In particular, the present invention contemplates testing of individuals who show a high risk profile for polymorphisms at the interleukin 1$\alpha$ and 1$\beta$ genes for factors regulating immunoglobulin production, and in particular, production of IgG2 antibodies. See generally, H. A. Schenkein, "Genetics of Early-Onset Periodontal Diseases," In: Molecular Pathogenesis of Periodontal Disease (1994 ASM, Robert Genco, Ed.). The data below sets forth the ranges for IgG2 antibodies (provided in micrograms per milliliter) for individuals of different periodontal heath status.

| | A. Afro-Americans | | |
|---|---|---|---|
| | Healthy | LJP | G-EOP |
| Mean | 4312 | 5241 | 4548 |
| SD | 1749 | 2032 | 2091 |
| Range | 676–10,600 | 1650–12,500 | 676–12,000 |

| B. Non-Afro-Americans | | | |
|---|---|---|---|
| | Healthy | LJP | G-EOP |
| Mean | 3216 | 4051 | 3463 |
| SD | 1612 | 1894 | 1509 |
| Range | 676–10,200 | 1690–9,300 | 676–8,000 |

While it is not intended that the present invention be limited to any particular theory, it is believed that healthy individuals, upon challenge by periodontally-relevant bacteria, are able to mount a high level IgG2 response, thereby stopping the disease before it can become severe. In this regard, the above table shows that, regardless of race, the LJP group has elevated levels. On the other hand, those individuals who, upon exposure to bacteria, are not able to mount a high level response cannot block the progression of the disease to a more severe form. In this regard, the above table shows that, regardless of race, the G-EOP group shows antibody levels that are the same as individuals who are healthy.

With the above considerations, the present invention contemplates that additional testing can further assist the clinician with periodontal disease management. Healthy individuals who show a high risk profile for polymorphisms at the interleukin 1α and 1β genes who also show depressed levels of IgG2 antibodies (i.e. levels less than approximately 3000 for Afro-Americans, and levels less than approximately 2000 for Non-Afro-Americans) would be expected to be at increased risk of developing the more severe form of periodontal disease (G-EOP). Such individuals showing such results for both testing schemes would be candidates for early intervention and careful monitoring (discussed below).

F. Post-Testing Treatment

The availability of a reliable diagnostic method for EOP, such as now provided by the present invention, greatly enhances both the prognostic ability of practitioners and the management of presymptomatic patients with this disease. In prepubertal patients, who are not yet old enough to express the disease, the test can be used in a predictive manner to establish the level of risk in such patients. This is of particular importance in EOP due to rapid progression of these diseases. A positive test would provide the rationale for the following:

1. Frequent dental visits to monitor for disease onset.
2. Aggressive preventive measures to reduce the progression or severity of disease.
3. Presymptomatic antibacterial therapy, possibly to include bacterial monitoring and antibiotic, mechanical, or other appropriate therapy to eliminate or reduce bacterial pathogens in plaque.
4. In patients with localized forms of EOP, aggressive intervention via surgical therapy and/or antibiotic management. (Since the test appears to particularly apply to the generalized forms of EOP, patients with LJP who are found to be at risk for progression to generalized EOP would benefit from aggressive therapy and careful scrutiny of as yet unaffected sites)
5. Therapy aimed at reconstruction of the lost tissues, such as bone grafting and guided tissue regeneration, could be planned, delayed or excluded based upon the prediction of further likelihood of bone loss by the genetic test.
6. Rationale for aggressive management of other disease risk factors, such as cigarette smoking, would be provided.
7. Many patients in this age range are candidates for orthodontic therapy. Patients with family histories of severe periodontitis at an early age would benefit from testing to guard against the possibly serious consequences of such therapy in the presence of EOP.

Importantly, many diseases have been found to actually consist of a mixture of genetic subtypes with different basic causes. These genetic subtypes often respond very differently to alternative therapeutic strategies. The present invention offers the chance to identify subtypes and correlate treatment results so as to provide a means to determine the optimal therapy for each subtype and thus to improve clinical treatment outcome.

Experimental

The following describes the work showing the above-discussed correlation between particular polymorphisms and periodontal disease. The study was designed to capitalize on a new method of genetic epidemiology known as the transmission disequilibrium test (TDT). This method employs a family-based experimental design to avoid potential pitfalls due to mismatching of case and control groups or admixture of subpopulations consisting of different racial or ethnic groups. In addition, theoretical analyses indicate that this approach may be much more powerful than traditional linkage-based approaches for detecting alleles of relatively small effect such those conferring a 2-fold or 4-fold increase in disease risk.

The study involved characterizing IL-1α and IL-1β polymorphisms for DNA samples from a collection of EOP families, and used the TDT to evaluate these data. The effect of smoking was considered, as well as the relationship between the IL-1α and IL-1β polymorphisms to each other, to attempt to determine which of these two genetic variants may be more strongly associated with the disease.

A. Materials and Methods

1. Identification Of Smokers

To determine which of the subjects were smokers at the time of examination, serum levels of cotinine were analyzed; cotinine is a stable primary metabolite of nicotine. Serum cotinine was measured by double antibody radioimmunoassay (Double Antibody Nicotine Metabolite, Diagnostic Products Corporations). The distribution of serum levels of cotinine in the subject population was bimodal, with a large group of subjects with levels <50 ng/ml. These distributions were used to empirically establish conservative cutoff values for non-smokers as $\leq 25$ ng/ml and $\geq 75$ng/ml for smokers. Individuals with intermediate levels of cotinine were classified as smoking status unknown and excluded from analyses involving smoking.

2. Multiplex EOP Families

Probands for this study were referred to the Clinical Research Center for Periodontal Disease from School of Dentistry Clinics at Virginia Commonwealth University or by practicing clinicians in the Richmond, Va. area and surrounding counties. Subsequently, family members were identified and recruited. The 35 families participating in this study included 107 African American subjects with EOP (94 with DNA), 99 unaffected African Americans (85 with DNA), 34 Caucasian subjects with EOP (31 with DNA), and 45 unaffected Caucasian subjects (36 with DNA). These families were chosen for participation based upon the finding of multiple cases of EOP within the first, second or third degree relatives of the proband (multiplex families).

Tentative family pedigrees were established based upon information from family members; such pedigrees were modified if necessary following verification following DNA analyses (see below). Each subject received a complete periodontal evaluation which included assessments of pocket depth, attachment loss, plaque index, gingival index, bleeding upon probing, and suppuration. Measurements were performed at 4 sites per tooth (mesiobuccal, midbuccal, distobuccal, and midpalatal). At the time of the examination, a blood sample was taken and processed for DNA and establishment of EBV-transformed cell lines.

EOP probands were initially diagnosed with either a localized (LJP) or generalized (G-EOP) form of disease as described below. All available family members were clinically assessed and assigned a periodontal diagnosis of LJP, G-EOP, adult periodontitis (AP), or periodontal health (HP). Family members under the age of 12 were not included in this study unless they exhibited a form of EOP. The diagnostic criteria for non-proband family members were of necessity slightly different than for probands in order to both accurately identify EOP probands (thus applying very stringent diagnostic criteria) and to subsequently allow diagnosis all other individuals within that family as accurately as possible. In cases where family members with periodontitis were beyond the arbitrary age limits imposed for the EOP diagnostic categories, diagnoses of EOP were based upon historical information as well as radiographic evidence if available. In such cases, the clinician performing the examination utilized available data to assign a clinical diagnosis of adult periodontitis with a "% likelihood" that the patient was previously affected with EOP. For this analysis, only cases in which the clinician assigned >50% likelihood of previous EOP (which required compelling historical or radiographic data) were included in this category. AP and edentulous subjects assessed as having a >0% but <50% likelihood of previous EOP were conservatively classified as "diagnosis unknown" for all statistical analyses. Patients were categorized according to the following criteria:

Healthy Periodontium (HP): Subjects of any age with no evidence of attachment loss (AL) at more than one site, or pockets greater than 3 mm, i.e. who have no detectable periodontitis.

Adult Periodontitis (AP): Subjects of age >25 years; with AL 2 mm or greater in any extent or severity pattern on more than one tooth. In subjects less than 35 years old AL must have appeared to have been consistent with plaque levels, other local contributing etiologic factors, and age, with less severe attachment loss than in LJP or G-EOP, or with an indication of adult onset. Further, the distribution (extent) of the disease was such as to not suggest localization to first molars and incisors, nor related to teeth affected by trauma, endodontic disorders, or other determinable local etiology other than periodontitis.

Localized Juvenile Periodontitis (LJP): For probands, subjects with disease of onset from puberty up to age 30 with at least 4 mm AL on at least 2 permanent first molars and incisors (at least one molar must have been affected) and no more than 2 teeth which were not first molars or incisors that were affected by 5 mm AL or more. For family members of probands, severity of AL may have been less than 4 mm but with a minimum of 2 mm at affected molars and incisors.

Generalized Early-onset (Rapidly Progressive, Generalized Juvenile) Periodontitis (G-EOP): For probands, subjects with disease onset up to age 35 with at least 8 teeth affected (5 mm AL or more), at least 3 of which were not first molars and incisors. For family members of probands, attachment loss at multiple sites must have been 3 or 4 mm; however, AL must have indicated that the pattern is more excessive than would be likely for adult periodontitis.

3. Laboratory Assays

DNA was extracted from peripheral blood following hypertonic sucrose cell lysis using proteinase K digestion and alcohol precipitation methods. See generally, Bell et al., "Polymorphic DNA region adjacent to the 5' end of the human insulin gene," *Proc. Natl. Acad. Sci. USA* 78:5759 (1981). In some cases, immortalized cell lines were established by EBV transformation of subjects' lymphocytes, and these were used for DNA extractions. DNAs were amplified via the polymerase chain reaction in two separate reactions using oligonucleotide primers designed to amplify either portions of the IL-1a gene surrounding the IL-1A −889 polymorphic site or the IL-b gene surrounding the IL-1B +3953 polymorphic site (as described above). PCR conditions consisted of 60 ng of template genomic DNA, 200 $\mu$M of dNTPs, 2 mM $MgCl_2$, 1× concentration of the reaction buffer supplied by the manufacturer with 0.3 U of Amplitaq (Perkin Elmer, Inc.) thermostable DNA polymerase and 3 picomoles of each primer in a volume of 15 $\mu$L. Amplifications were performed for 10 cycles of 94° C. denaturing for 15 sec, 55° C. annealing for 15 sec, and 72° C. for 30 sec; 20 additional cycles with the same parameters except denaturing at 89° C. (to retain polymerase activity); followed by a final extension period at 72° C. for 10 min. PCR products were diluted 1:20 with water and 2 $\mu$L of each diluted product were incubated overnight in a total volume of 10 $\mu$L with the buffers supplied by the enzyme manufacturers at 37° C. with 10 U of Nco I for the IL-1A −889 fragment and at 65° C. with 20 U of Taq I for IL-1B +3953. One of the oligonucleotide primers for each PCR reaction had been synthesized using a FAM phosphoramadite, so the PCR products could be analyzed using fluorescence-based detection. The restriction endonuclease digestion products were sized by denaturing PAGE on Applied Biosystems (Perkin Elmer, Inc.) Model 373 automated DNA analyzers with GENESCAN software (Applied Biosystems, Inc.) as described by Ziegle et al., "Applications of automated DNA sizing technology for genotyping microsatellite loci," *Genomics* 14:1026 (1992). For the IL- 1A −889 polymorphism the digestion product of 83 bp was designated allele 1, while the 99 bp fragment (lacking the polymorphic restriction site) was designated allele 2. For the IL-1B +3953 polymorphism, the digestion product of 85 bp was designated allele 1, while the 182 bp fragment (lacking the polymorphic restriction site) was designated allele 2. These allele designations are consistent with those used previously by Kornman et al. (1997) in their study of adult periodontitis.

4. Statistical Analyses

African American families and Caucasian American families were evaluated both separately and combined, and also evaluated LJP and G-EOP subtypes of EOP both separately and combined for all analyses. Linkage disequilibrium between EOP and IL-1 polymorphisms was assessed using the transmission disequilibrium test (TDT). The test counts numbers of transmissions of allele 1 versus allele 2 from heterozygous parents to affected offspring. Under the null hypothesis that the polymorphic marker has no effect on disease risk, the two alleles are expected to be transmitted with equal frequency. Deviation from the 1:1 expected ratio of transmission indicates that the marker is in linkage disequilibrium with the disease. This means that the marker polymorphism itself, or another variable DNA site in very close proximity to the marker influences risk of the disease. The computer programs SIBPAIR Version 0.92, TRANSMIT, and TDTEX Release 3.0 (S.A.G.E., 1997) were used to perform these analyses. Most tests were performed using SIBPAIR, except as otherwise indicated, because this program uses permutation methods to robustly estimate P-values for small sample sizes. It is possible that biased transmission to affected offspring might be unrelated to disease risk, due either to an artifact of the molecular assay (such as partial digestion by restriction enzymes) or meiotic drive (caused, for example, by an embryonic lethal gene in the vicinity of the marker). These confounding alternatives were addressed by also performing the TDT for unaffected offspring, who would be expected to exhibit the same levels of biased transmission as affected offspring if the bias was due to these alternative, non-disease related mechanisms.

IL-1 genotype frequencies were compared in the affected versus the unaffected members of the multiplex families using the SAS System for Windows Release 6.11 (SAS Institute, Inc.). Other miscellaneous data manipulations and statistical tests such as Fisher's Exact test and Logistic Regression used for these analyses were also performed using the SAS program.

Since the IL-1A and IL-1B markers are located so close together on the chromosome it is possible that the alleles at their respective marker polymorphisms are correlated. This means, for example, if a chromosome contains a 1 allele at the IL-1A marker, it may be highly likely to contain a 1 allele at the IL-1B marker. This is important information that is necessary to distinguish whether IL-1A, IL-1B or both polymorphisms are responsible for influencing EOP risk. First, confirmation that these two IL-1 polymorphic markers are located very close to each other was made by performing LOD score linkage analysis using the computer program MLINK. Next, maximum likelihood methods implemented in the program 3LOCUS.PAS were used to evaluate linkage disequilibrium between the two marker polymorphisms in the African American and Caucasian American subjects. These analyses were performed separately for affected and unaffected subjects to avoid any confounding between disequilibrium with the disease and disequilibrium between the two markers. This method requires collections of unrelated individuals, so all members of the families were first identified who were biologically unrelated (i.e., founders and spouses who married into the family).

SAS programs were used to identify haplotypes of the IL-1A and IL-1B markers. As noted above, a haplotype refers to a combination of the alleles at the two markers contained on a single chromosome. A chromosome might have a 1 allele at the IL-1A marker and a 1 allele at the adjacent IL-1B marker position, or any of the other three possible combinations (1 and 2, 2 and 1, or 2 and 2, respectively). TDT analyses was then repeated using the two locus combined haplotypes to assess the relative importance of the IL-1A versus the IL-1B markers for EOP disease risk.

To assess evidence of linkage to EOP for each of the IL-1 markers separately, as well as for their combined haplotypes, two sibpair tests were conducted. Affected sibpair tests and concordant/discordant sibpair regression tests were performed using the computer programs SIBPAIR Version 0.92 and SIBPAL Release 3.0 (S.A.G.E, 1997). The affected sibpair test focuses on affected siblings only. This is done because of the concern that some diseases gene carriers may not express the disease (incomplete penetrance) which means that unaffected individuals may or may not be gene carriers. By contrast, affected siblings are assumed to both be disease gene carriers even in the presence of incomplete penetrance, so a linkage test limited to affected sibling pairs only may be more powerful. The affected sibpair test evaluates whether, for the entire set of families under study, pairs of affected siblings share more than 50% of marker alleles identical by descent (IBD, i.e., commonly inherited from the same parent). Under the null hypothesis that the marker has no influence on disease risk, siblings will share 50% of their alleles IBD. However, if a disease gene that the affected pairs of siblings share is located near a polymorphic marker locus, this increases allele sharing above the null hypothesis 50% value. The concordant/discordant sibpair regression test is an extension of this strategy to include unaffected siblings. It may be especially applicable for diseases with some non-genetic causes (phenocopies) and/or where several different, unlinked disease-predisposing genes cause the same clinical phenotype. In other words, sometimes one affected sibling may have the disease due to a particular gene while the other affected sibling may have gotten the disease via non-genetic factors or due to some other, unlinked gene. Under these circumstances, pairs of affected siblings may be no more reliable for inferring disease gene carrier status than pairs of unaffected siblings, so investigators would be wise to utilize information from all kinds of siblings. The regression test evaluates whether allele sharing is above 50% IBD at a putative disease-linked marker for pairs of siblings which are the same with respect to their disease status (i.e., pairs of affected siblings and pairs of unaffected siblings). These are called concordant pairs and their level of IBD allele sharing is contrasted to the allele sharing for pairs of siblings where one is affected and the other unaffected (discordant pairs). Discordant sibling pairs are expected to share less than 50% of their alleles IBD at a marker locus close to a disease gene. The significance test evaluates whether the slope of mean IBD sharing for concordant versus discordant sibling pairs is negative.

B. Results

Figure 2:
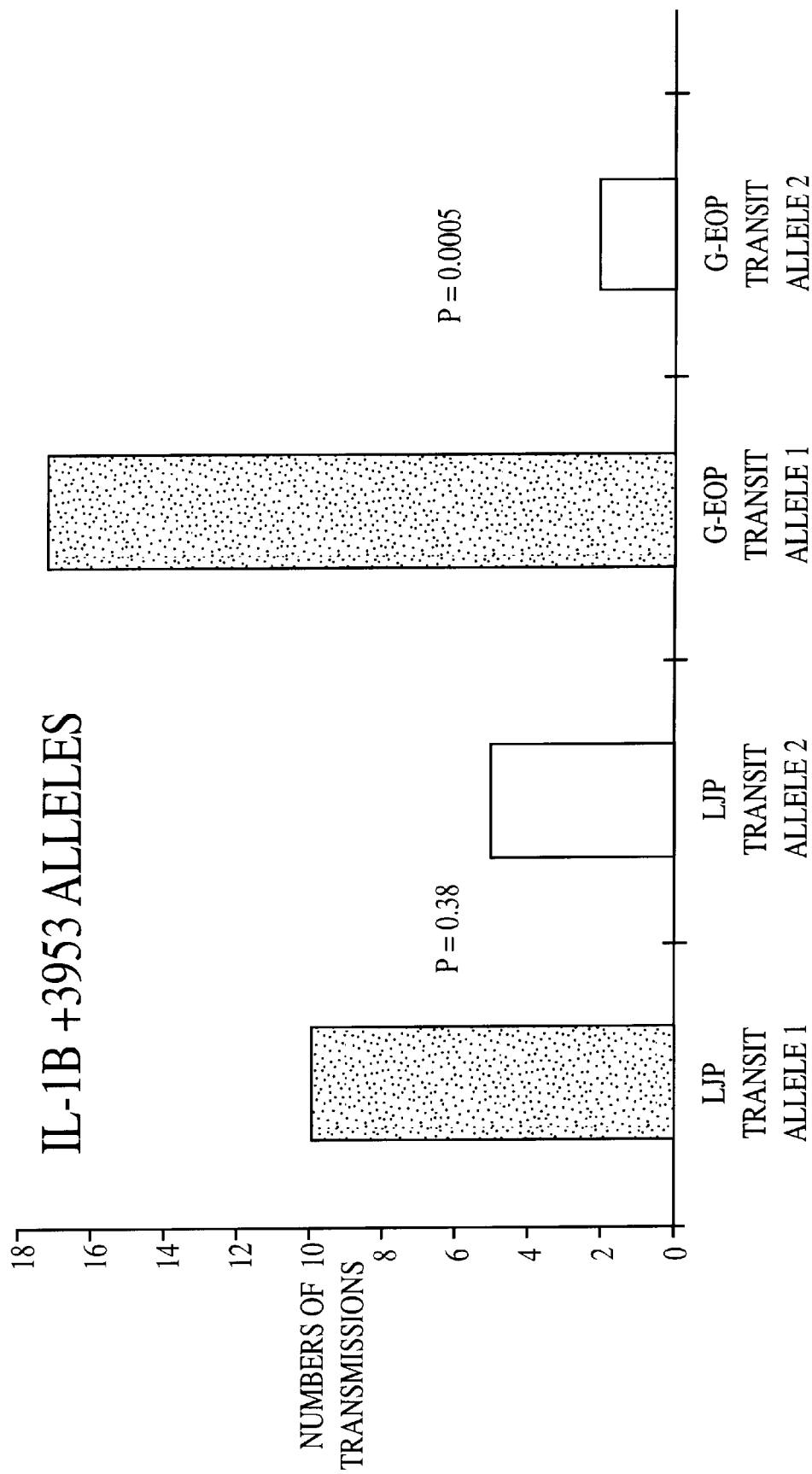
FIG. 2 is a graph showing that allele 1 of the IL-1B +3953 marker is transmitted significantly more often than allele 2 to G-EOP affected individuals.

The study revealed that allele 1 of the IL-1A −889 marker was transmitted significantly more often (P=0.0065) than allele 2 to G-EOP affected individuals when analyzed using the SIBPAIR program to empirically estimate P-values (FIG. 1). A similar trend was also found for LJP subjects, but was not statistically significant. Evidence of disequilibrium for allele 1 of the IL-1B +3953 marker was even stronger for the G-EOP cases (FIG. 2; P=0.0005), with 17 transmissions of the allele 1 and only 2 transmissions of allele 2 (versus a null hypothesis expectation of a 1:1 ratio of transmissions of each allele). Allele 1 at the IL-1B marker was also transmitted more often than allele 2 for LJP cases but this asymmetry was not statistically significant. These findings were confirmed by re-analyses using two other computer programs implementing similar but not identical algorithms designed to assess transmission disequilibrium. The TDTEX program is highly conservative in that it excludes all cases where genotype information is available for only one parent. For the data this yields a ratio of 12 transmissions of allele 1 and 1 transmission of allele 2 at the IL-1B +3953 marker for G-EOP cases (P=0.003) and weaker support for transmission disequilibrium at the IL-1A −889 polymorphism (P=0.024). A third algorithm uses maximum likelihood methods to estimate the probability distribution of genotypes for missing parents was implemented using the program TRANSMIT. This analysis provided strong rejection of the null hypothesis of transmission equilibrium for G-EOP cases for the IL-1B +3953 polymorphism ($X^2$=12.3, 1 df, P<0.001), with borderline statistical significance for the IL-1A −889 maker ($X^2$=4.7, 1 df, P<0.05) and no evidence of disequilibrium for LJP cases. To be sure that the biased transmission observed is related to periodontal disease and not an artifact of the molecular assay or due to meiotic drive associated with this portion of chromosome 2, transmission disequilibrium was evaluated in unaffected offspring. No evidence was found whatsoever of biased transmission for any of the tests focused on unaffected offspring. For example, for the IL-1B +3953 marker 13 transmissions of allele 1 and 10 transmissions of allele 2 were observed (P=0.51) using the SIBPAIR program, 8 transmissions of allele 1 and 10 transmissions of allele 2 were observed using the TDTEX program (P>0.05), and a $X^2$=0.02, 1 df, P>0.05 using the TRANSMIT program.

TABLE 1

Transmission Disequilibrium by Smoking Status

| Diagnosis[1] | Smoking Status[2] | IL-1A-889 T 1[3] | IL-1A-889 T 2 | IL-1B + 3953 T 1 | IL-1B + 3953 T 2 |
|---|---|---|---|---|---|
| LJP | N | 9 | 5 | 8 | 0 |
|  | Y | 3 | 3 | 1 | 1 |
|  | Y + N + U | 18 | 12 | 10 | 5 |
| G-EOP | N | 11 | 4 | 9 | 1 |
|  | Y | 7 | 2 | 5 | 0 |
|  | Y + N + U | 24 | 8 | 17 | 2 |

[1]LJP, juvenile periodontitis = localized early onset periodontitis; G-EOP, rapidly progressive, generalized juvenile periodontitis.
[2]Non-smoker (N) defined as ≦25 ng/ml serum cotinine; Smoker (Y) defined as ≧ 75 ng/ml serum cotinine; individuals with intermediate cotinine levels classified as unknown (U) smoking status.
[3]Numbers of transmissions from heterozygous parents of the 1 or the 2 allele to affected offspring.

Disequilibrium between G-EOP and the IL-1B +3953 polymorphism was of approximately equal magnitude in smokers and non-smokers (Table 1). For non-smoking LJP cases, the difference between the 8 transmissions of allele 1 versus 0 transmissions of allele 2 is statistically significant (P=0.0085).

Figure 3:
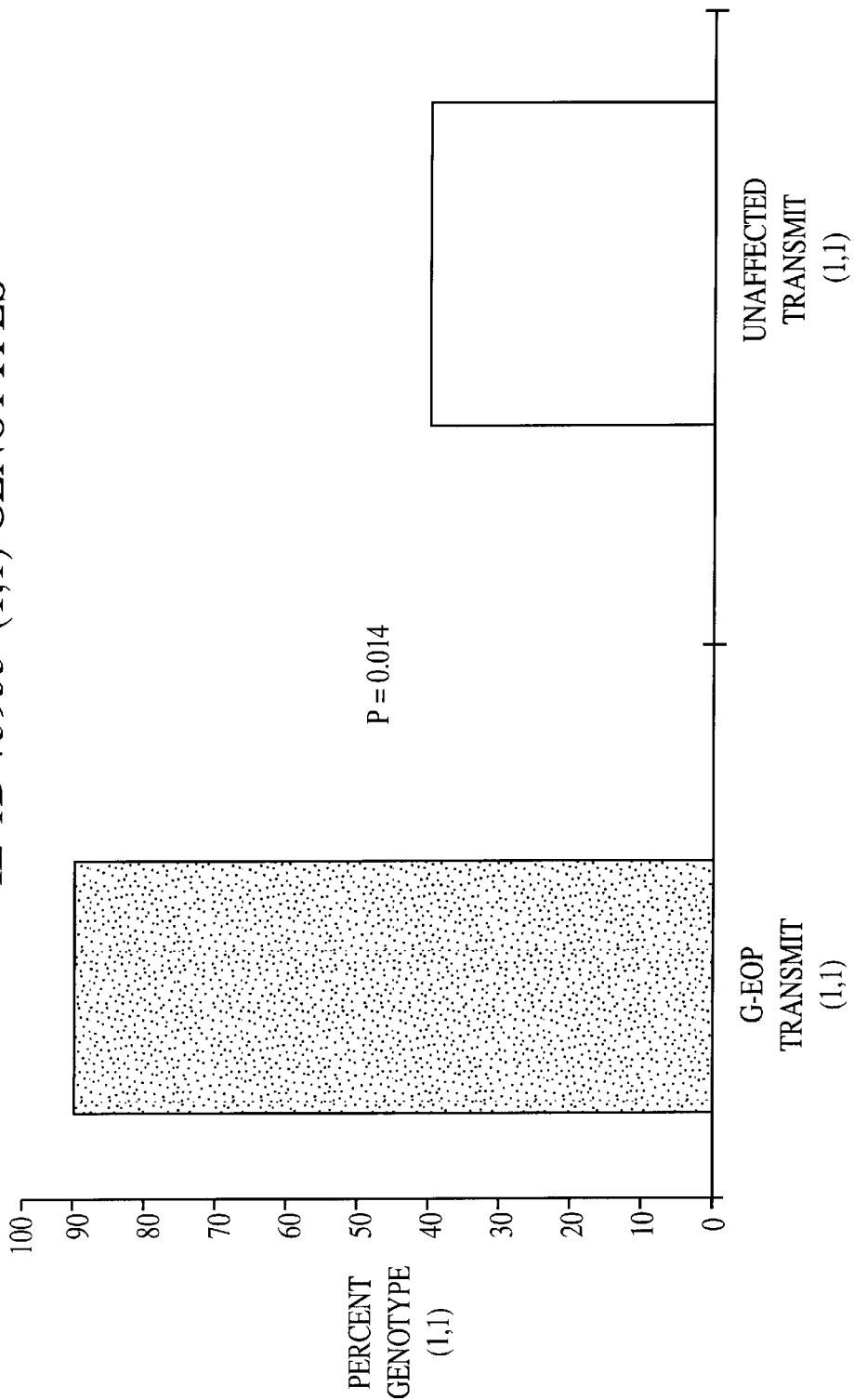
FIG. 3 is a graph showing that the (1,1) IL-1B +3953 genotype is transmitted to G-EOP affected subjects 92% of the time which is significantly greater than the frequency of transmission to unaffected subjects.

Since individuals exist in the population as genotypes and not as individual alleles, a disequilibrium analysis was performed at the genotype level. The (1,1) homozygous genotype is known to be by far the most common (frequencies reported below). Most of the other individuals are of the (1,2) genotype, while the (2,2) homozygote is quite rare (<3%). The allelic TDT was extended to the genotype level and it was found that the (1,1) IL-1B +3953 genotype is transmitted to G-EOP affected subjects 92% of the time versus a frequency of transmission of only 40% to unaffected subjects (FIG. 3). This contrast is statistically significant (Fisher's Exact Test, two-tailed, P=0.014). Because (1,1) homozygotes differ from (1,2) heterozygotes in transmission frequency, one can conclude that the 1 allele isn't dominant over the 2 allele. However, since (2,2) homozygotes occur so rarely, one can't determine whether this genotype differs in EOP risk compared to the (1,2) heterozygote.

The transmission disequilibrium for G-EOP cases was of approximately equal magnitude in Caucasian and African American subjects. At the IL-1B +3953 polymorphism, transmissions were observed of allele 1 and allele 2 of 7 and 1, respectively, for Caucasian subjects and 10 and 1 for African American subjects. The (1,1) genotype was more frequent (71%) in African American family members (including both affected and unaffected subjects) compared to Caucasians (54%). The higher frequency of this G-EOP associated allele in African American subjects is consistent with the higher prevalence of EOP in this population. Due to the highly complex network of correlations among family members it is not feasible to assess the statistical significance of genotype frequency differences between G-EOP affected subjects and unaffected relatives in the two racial groups. To perform this statistical test, founders and other unrelated members of the collection of families were selected, and a 2×2×2 logistic regression analysis was performed of the frequencies of the (1,1) versus (1,2)+(2,2) genotype groups in G-EOP affected versus unaffected subjects, in the Caucasian versus the African American groups. These genotype frequencies for unrelated subjects identified at random from within the collection of families are presented in FIG. 4. The logistic regression results indicate significant differences between the races and between G-EOP and unaffected subjects. The conclusion that the IL-1B association with G-EOP is consistent across both races; this is supported by the fact that teh Race X Affection Status parameter in the logistic regression model is not significant. When considering all family members, a (1,1) genotype frequency difference was observed of about 16.6% between G-EOP affected and unaffected subjects. This was very nearly as large as the difference of 17.6% found when the frequencies of the two-locus combination of IL-1A and IL-1B markers specified by Kornman et al. (discussed above) were contrasted for G-EOP affected versus unaffected family members. This is consistent with the TDT findings indicating that variation at the IL-1A marker is secondary to that found at the IL-1B +3953 site.

Additional tests were performed which were aimed at further establishing whether genetic variation at the IL-1α gene or the IL-1β gene is the actual source of the association with EOP disease risk. Since these genes are known to reside approximately 50 kbp apart on the chromosome, it is quite possible that the alleles at the two markers may be closely correlated with each other (i.e., in disequilibrium). If the correlation was close to 1.0, it would be impossible to distinguish which marker was more related to disease risk, since they would each give precisely the same evidence of association. As presented above, different TDT results were obtained for the two markers, so one knows that they are not in complete disequilibrium, but it remains possible that they may be partially correlated. First, LOD score linkage analysis was performed between the two markers (assuming each is a fully penetrant codominant system). A very highly significant LOD score was obtained of 7.84 maximizing at a recombination fraction of 0.0. In addition to confirming the two markers very close linkage, this finding validates the marker typing and pedigree structures. We used maximum likelihood methods to estimate the extent of linkage disequilibrium between the two populations. We found highly significant evidence of disequilibrium between the IL-1A and IL-1B polymorphic sites in the Caucasian population (permutation based P=0.0013). The haplotypes with 1 alleles at both markers or with 2 alleles at both markers occurred about 60% and 28% of the time, respectively, which is substantially elevated above their expected frequencies under linkage equilibrium of 44% and 11%. Linkage disequilibrium isn't complete in the Causcasian population, since we extimated that the mixed haplotypes of 1 and

TABLE 2

Haplotype Analyses of G-EOP Subjects

| Informative Marker[1] | T 1[2] | T 2 |
|---|---|---|
| IL-1A-889 only | 9 | 7 |
| IL-1B + 3953 only | 7 | 1 |
| Both A-889 & B + 3953 | 8 | 1 |

[1] One or both parents of affected offspring is (are) heterozygous for the marker polymorphism and transmission to the offspring can be unambiguously inferred.
[2]Numbers of transmissions from heterozygous parents of the 1 or the 2 allele to affected offspring.

2 alleles at the two markers occur about 11% of the time. By contrast, no significant evidence of disequilibrium was observed in the African-American population, although there was a small excess (about 45%) of 1/1 and 2/2 haplotypes.

Since disequilibrium between IL-1A −889 and IL-1B +3953 is incomplete, tests were performed to distinguish which of the two polymorphisms is more closely correlated with EOP. To do this, the genotypes at the two IL-1 loci were converted into two-locus haplotypes, and the TDT analyses was repeated using the haplotypes instead of alleles at a single locus. As shown in Table 2, these analyses indicate that transmission disequilibrium is primarily associated with the IL-1B +3953 genetic polymorphism. When a parent varies only at the IL-1A −889 site, transmission of allele 1 versus allele two is approximately equal (9 versus 7 transmissions, respectively). In contrast, when a parent is heterozygous at the IL-1B +3953 site only, allele 1 is transmitted 7 times and allele 2 only once. The contrast of the 9:7 transmission ratio for IL-1A −889 only versus the 15:2 ratio for IL-1B with or without IL-1A heterozygous is of borderline statistical significance (Fisher's Exact Test, two-tailed, P=0.057). Thus, it appears that the IL-1B +3953 variation may be most important in influencing risk of this disease. Results of the affected sib pair and regression non-parametric linkage analyses using the IL-1A and IL-1B combined haplotypes are presented in Table 3. Similar results were found for analyses of each marker separately (data not shown). Only marginally significant evidence was found of a single major gene for G-EOP risk in this chromosomal region, with elevation of allele sharing only present in pairs of unaffected siblings (P=0.008) and a nearly statistically significant regression statistic (P=0.061).

C. Conclusions

The finding of an association between genetic variation at a polymorphic site in the IL-1β gene and risk of G-EOP (and possibly also LJP) for the first time definitively demonstrates that an important genetic component underlies the etiology of this disease. For many years, it has been recognized that EOP "runs in families" and formal segregation analyses have suggested the possible existence of a gene or genes of major effect. These observations, however, could not rule out the possibility that some component of the family environment, such as diet, oral hygiene, or transmission of virulent biotypes of bacteria might

TABLE 3

Linkage Analysis of G-EOP with IL-1 Halotypes

| Sibling Pair Type[1] | # Pairs | % IBD[2] | P-Value |
| --- | --- | --- | --- |
| Affected/Affected | 44 | 50.4 | 0.457 |
| Unaffected/Unaffected | 29 | 60.3 | 0.008 |
| Affected/Unaffected | 43 | 47.2 | 0.221 |
| Regression Analysis[3] | N/A | N/A | 0.061 |

[1]Pairs of full siblings where either both are affected (concordant), both unaffected (concordant) or one is affected and the other unaffected (discordant).
[2]Percentage of parental alleles shared by the sibling pairs of each type that have been inherited identical by descent.
[3]Test of whether the mean % IBD for the concordant sibling pairs is higher than for the discordant pairs.

explain aggregation of the disease in family members. The use of the transmission disequilibrium test strategy rules out these non-genetic alternatives. The TDT approach for family-based experimental designs also eliminates false positive associations which might occur in case-control designs due to imperfect matching or due to the presence of racial or ethnic subgroups within the population.

The finding of IL-1B disequilibrium with EOP differs in several major ways from the finding reported by Kornman et al. (discussed above) regarding severity of adult periodontitis. Most important, we found EOP strongly associated with allele 1 at this locus, while they reported severity of adult periodontitis was associated with allele 2. Thus, for diagnostic or prognostic purposes, the data discussed above indicate a completely opposite conclusion regarding the identification of individuals at increased risk of disease. Second, while the finding of Kornman and colleagues was limited to non-smokers, the association herein described with EOP appears to apply to both smoking and non-smoking subjects. Third, the data indicate an effect in both Caucasian and African American subjects, while the previous study's conclusions were limited to Caucasians of Northern European heritage. Fourth, the data indicate that the IL-1B polymorphism is more important than the IL-1A variant, while the previous study suggested both markers were associated with adult disease severity.

In the above-described study, three slightly different TDT tests were applied to the analyses of the data using three different computer programs. These programs differ in how they handle families with only one parent available for genotyping. This can be important for some (rare) circumstance where a very common allele might exhibit false positive evidence of transmission disequilibrium. First, SIB-PAIR was run using an option which ignores this possibility and fully utilized all available data for the families, but consequently increased the chance of false positives. TDTEX deletes all families with a missing parent, and, therefore, is conservative but suffers a considerable loss of power for data sets such as ours where frequently only one parent is available for genotyping. TRANSMIT uses maximum likelihood methods to estimate the probability distribution of the missing parental genotypes, thus potentially eliminating false positives while retaining power. This latter method does require making assumptions about the reliability of marker allele frequency estimates derived from the collection of families under study. Since the findings are confirmed by all three methods, however, it is believed that the results are highly reliable.

In the course of these analyses multiple statistical tests were performed, including disequilibrium for both LJP and G-EOP, in African American and Caucasian subjects and in the combined data set for both races, for IL-1A and IL-1B markers and their haplotypes, and (for some of the tests) using the three alternative methods of accounting for missing parents just noted above. Clearly, some adjustment for these multiple comparisons is warranted. However, many of the tests are very highly correlated. For example, the three TDT methods that differ in the way they account for missing parents produce very similar results, the polymorphisms at IL-1A and IL-1B are themselves partially correlated, and the data set pooling results for both racial groups is highly correlated with the outcomes found in each race analyzed separately. Consequently, a simple Bonferroni adjustment would be inappropriate since it would produce P-values that were biased in a very overly conservative direction. In lieu of making such adjustments, it is noted that the most significant finding of disequilibrium between the IL-1B marker and G-EOP (with nominal P=0.0005) is robust to a Bonferroni adjustment equivalent to 100 independent statistical tests, far more than actually performed in this study.

If the TDT is applied using only simplex families (one affected offspring per family) a significant transmission bias can only be caused by linkage disequilibrium. However, a positive TDT finding using multiplex families could potentially be caused by linkage only, without any linkage disequilibrium. This means that there could be a disease gene in the vicinity of the marker, but that no one marker allele is associated with the disease in the population. Thus, in one family the disease may "travel" with allele 1, while in another family with allele 2. The artifactual appearance of allelic association could conceivably be attributable to the analysis of multiple affected relatives in the same (very large) families where all relatives happened to be linked to the same disease allele. Such a finding of linkage would still be of great value in that it maps a disease gene to a chromosomal region. However, the size of the candidate region where the gene might be located under a finding of linkage could potentially be much larger (ca. 20–30 Mbp) than if the finding is attributable to linkage disequilibrium (<<1 Mbp for outbred populations).

Since only weak or no evidence was found of linkage in the sib pair linkage test (Table 3), we conclude that our finding is, in fact, attributable to linkage disequilibrium rather than to linkage without disequilibrium. This means that the actual DNA variation which causes increased risk of EOP is either the IL-1B +3953 site or another site very close nearby.

Figure 4:
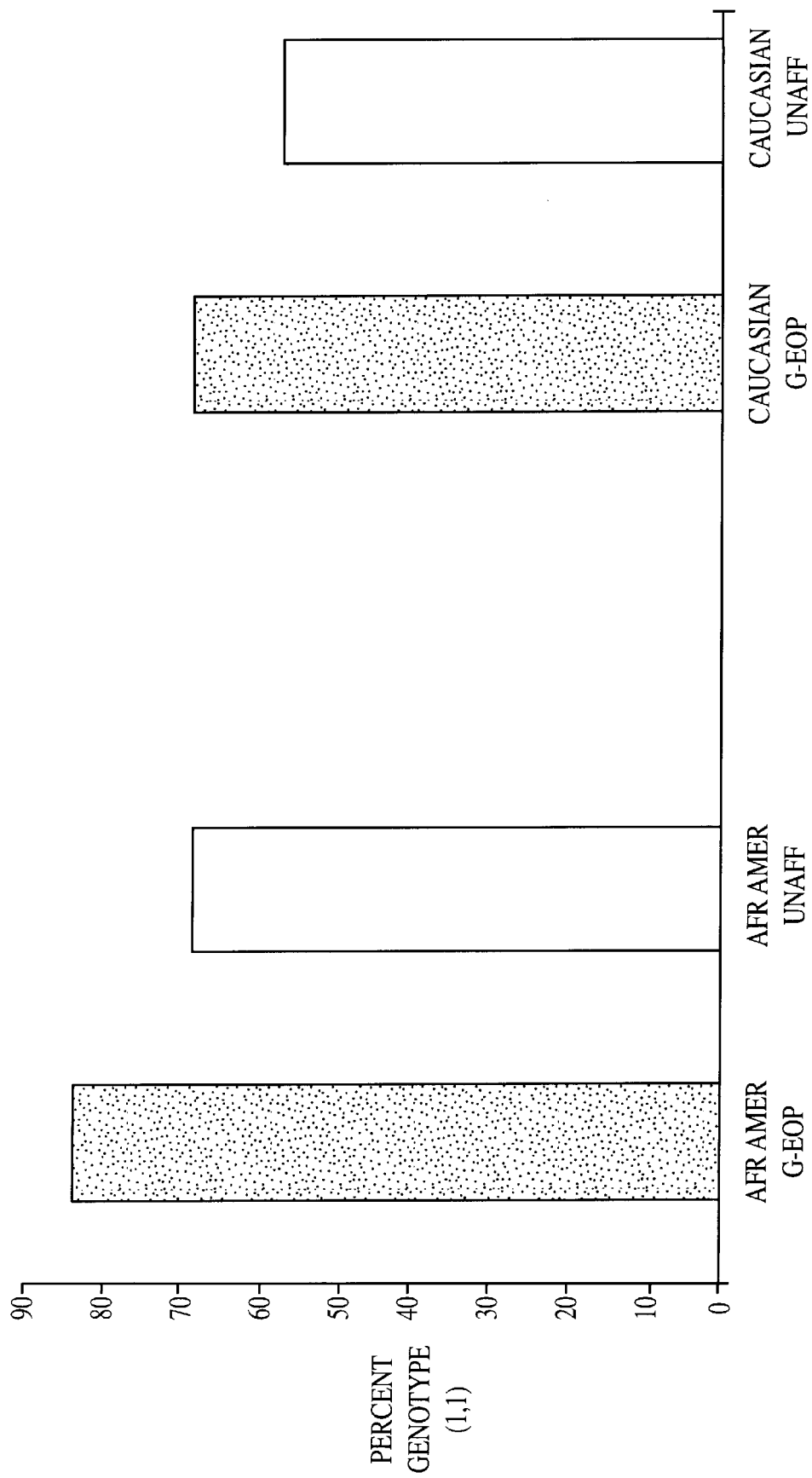
FIG. 4 is a graph showing IL-1B +3953 genotype frequencies by race and G-EOP disease status.

The evidence indicates that the IL-1B genetic variant doesn't act as a single major gene that accounts for all or nearly all of the difference among individuals in EOP risk. Instead, the finding of linkage disequilibrium without evidence of linkage is most consistent with an interpretation of EOP as a complex, oligogenic disorder, with IL-1 genetic variation contributing an important but not exclusive influence on disease risk. This is precisely the picture that has been emerging for other common diseases such as diabetes, many forms of cancer, cardiovascular diseases and mental illnesses. Unlike simple genetic diseases such as cystic fibrosis or muscular dystrophy, where inheriting the gene means getting the disease for certain, some EOP affected individuals may have the low risk IL-1B genotype and some unaffected individuals may have the high risk genotype (FIG. 4).

It is important to recognize, however, that the absence of a simple one-to-one mapping between disease gene and disease phenotype doesn't diminish the value of identifying these susceptibility genes. They still have great potential to explain a substantial portion of disease risk in the population and to predict risk for individuals. As discussed above, such knowledge can be applied to optimize health care resources by allocating greater monitoring and/or prophylactic treatment to individuals identified to be at high risk of developing the disease. Knowledge of disease etiology at the level of specific genes may also lead to improved therapies designed to correct the specific biochemical aberration caused by the gene defect. It may also be beneficial to classify subtypes of disease using a system based on gene defects rather than solely on differences in clinical presentation. Different therapies, in turn, might be most optimally targeted to the different gene defect subtypes of the disease. Finally, one of the biggest benefits that might accrue from identifying gene mutations in a complex disease such as EOP could be greatly enhanced power to understand the environmental components of disease etiology. Once one can adjust for the genetic sources of variation in disease risk by direct measurement of appropriate gene mutations, removal of this "noise" from studies should greatly enhance the ability to identify environmental influences on the disease.

What is claimed is:

1. A method of predicting a patient's susceptibility to generalized onset periodontal disease comprising:
   a) providing i) a sample from a patient, wherein said sample comprises nucleic acid, said nucleic acid comprising an IL-1B gene, and ii) a treatment means;
   b) treating said sample with said treatment means under conditions such that a high risk genotype for generalized early onset periodontal disease is detected if present, wherein said genotype comprises a genotype homozygous for allele 1 at the +3953 polymorphic site of said IL-1B gene; and
   c) detecting said high risk type genotype if present, wherein the presence of said high risk genotype is indicative of said patient's susceptibility to said generalized early onset periodontal disease.

2. The method of claim 1, where said sample is from a child suspected to be at risk for early-onset periodontal disease.

3. The method of claim 1, where said sample is from a young adult suspected to be at risk for early-onset periodontal disease.

4. The method of claim 1, wherein said sample is blood.

5. The method of claim 1, wherein said sample comprises epithelial cells.

6. The method of claim 5, wherein said nucleic acid is purified from said cells prior to said treating of step (b).

7. The method of claim 6, wherein said purified nucleic acid is amplified prior to said treating of step (b).

8. The method of claim 7, wherein said purified nucleic acid is amplified with primers which amplify said IL-1B gene.

9. A method of predicting a patient's susceptibility to generalized onset periodontal disease comprising:
   a) providing i) a sample from a patient, wherein said sample comprises nucleic acid, said nucleic acid comprising an IL-1A gene, and ii) a treatment means;
   b) treating said sample with said treatment means under conditions such that a high risk genotype for generalized early onset periodontal disease is detected if present, wherein said genotype comprises a genotype homozygous for allele 1 at the −889 polymorphic site of said IL-1A genes; and
   c) detecting said high risk type genotype if present, wherein the presence of said high risk genotype is indicative of said patient's susceptibility to said generalized early onset periodontal disease.

10. The method of claim 9, where said sample is from a child suspected to be at risk for early-onset periodontal disease.

11. The method of claim 9, where said sample is from a young adult suspected to be at risk for early-onset periodontal disease.

12. The method of claim 9, wherein said sample is blood.

13. The method of claim 9, wherein said sample comprises epithelial cells.

14. The method of claim 13, wherein said nucleic acid is purified from said cells prior to said treating of step (b).

15. The method of claim 14, wherein said purified nucleic acid is amplified prior to said treating of step (b).

16. The method of claim 15, wherein said purified nucleic acid is amplified with primers which amplify said IL-1A gene.

17. A method of predicting a patient's susceptibility to generalized early onset periodontal disease comprising:
   a) isolating nucleic acid from a patient; and
   b) detecting a high risk genotype for generalized early onset periodontal disease in said nucleic acid, if present, wherein said genotype is selected from the group consisting of genotypes homozygous for allele 1 at the +3953 polymorphic site of IL-1B, genotypes homozygous for allele 1 at the −889 polymorphic site of IL-1A, and a combination thereof, wherein said high risk genotype is indicative of said patient's susceptibility to said generalized early onset periodontal disease.

18. The method of claim 17, wherein said human is further tested for serum levels of IgG2 antibody.

19. The method of claim 17, wherein said nucleic acid is isolated from blood of said human.

20. The method of claim 17, wherein said nucleic acid is isolated from epithelial cells of said human.

21. The method of claim 20, wherein said nucleic acid is purified from said cells prior to said treating of step (b).

22. The method of claim 21, wherein said purified nucleic acid is amplified prior to said treating of step (b).

23. The method of claim 22, wherein said purified nucleic acid is amplified with primers which amplify said IL-1A gene and said IL-1B gene.

24. A method of predicting a patient's susceptibility to generalized early onset periodontal disease, comprising;
   a) providing:
      i) a sample from a patient wherein said sample comprises nucleic acid, said nucleic acid comprising IL-1A and IL-1B genes,
      ii) first and second reaction means,
      iii) first and second oligonucleotide primers capable of amplifying a region of said IL-1A gene, and
      iv) third and fourth oligonucleotide primers capable of amplifying a region of said IL-1B gene;
   b) reacting said first and second oligonucleotide primers with a first portion of said sample in said first reaction means under conditions such that a first amplification product of said IL-1A gene is produced;
   c) reacting said third and fourth oligonucleotide primers with a second portion of said sample in said second reaction means under conditions such that a second amplification product of said IL-1B gene is produced;
   d) treating said first and second amplification products under conditions such that a high risk genotype for generalized early onset periodontal disease is detected if present, wherein said genotype is selected from the group consisting of genotypes homozygous for allele 1 at the +3953 polymorphic site of said IL-1B gene, genotypes homozygous for allele 1 at the −889 polymorphic site of said IL-1A gene, and a combination thereof; and
   e) detecting said high risk type genotype if present, wherein the presence of said high risk genotype is indicative of said patient's susceptibility to said generalized early onset periodontal disease.

25. The method of claim 24, where said sample is from a child suspected to be at risk for early-onset periodontal disease.

26. The method of claim 24, where said sample is from a young adult suspected to be at risk for early-onset periodontal disease.

27. The method of claim 24, wherein said treating at step (d) comprises digesting said first and second amplification products with one or more restriction enzymes.

28. The method of claim 24, wherein said treating at step (d) comprises hybridizing a first pair of allele-specific oligonucleotide probe with said first amplification product and a second pair of allele-specific oligonucleotide probe with said second amplification product.

29. The method of claim 24, wherein said treating at step (d) further comprises:
   i) providing a first, second, third, fourth, fifth and sixth ligation oligonucleotides;
   ii) hybridizing said first, second and third ligation oligonucleotides with said first amplification product, under conditions such that at least two of said ligation oligonucleotides are ligated; and
   iii) hybridizing said fourth, fifth and sixth ligation oligonucleotides with said second amplification product, under conditions such that at least two of said ligation oligonucleotides are ligated.

30. The method of claim 28, wherein said first and second pairs of allele-specific oligonucleotide probes are labelled.

31. The method of claim 29, wherein at least two of said first, second and third ligation oligonucleotides are labelled, and wherein at least two of said fourth, fifth and sixth ligation oligonucleotides are labelled.

32. The method of claim 4, wherein said nucleic acid is purified from said blood prior to said treating of step (b).

33. The method of claim 32, wherein said purified nucleic acid is amplified prior to said treating of step (b).

34. The method of claim 33, wherein said purified nucleic acid is amplified with primers which amplify said IL-1B gene.

35. The method of claim 12, wherein said nucleic acid is purified from said blood prior to said treating of step (b).

36. The method of claim 35, wherein said purified nucleic acid is amplified prior to said treating of step (b).

37. The method of claim 36, wherein said purified nucleic acid is amplified with primers which amplify said IL-1A gene.

38. The method of claim 19, wherein said nucleic acid is purified from said blood prior to said treating of step (b).

39. The method of claim 38, wherein said purified nucleic acid is amplified prior to said treating of step (b).

40. The method of claim 39, wherein said purified nucleic acid is amplified with primers which amplify said IL-1A gene and said IL-1B gene.

* * * * *

```
                          SEQUENCE LISTING (1) GENERAL INFORMATION:

(iii) NUMBER OF SEQUENCES: 47

(2) INFORMATION FOR SEQ ID NO:1:

(i) SEQUENCE CHARACTERISTICS:
          (A) LENGTH: 140 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:1:

TTCATTTGCT AAGAGTCTGG TGTTCTACCA CCTGAACTAG GCTGGCCACA GGAATTATAA        60

AAGCTGAGAA ATTCTTTAAT AATAGTAACC AGGCAACAYC ATTGAAGGCT CATATGTAAA      120

AATCCATGCC TTCCTTTCTC                                                  140

(2) INFORMATION FOR SEQ ID NO:2:

(i) SEQUENCE CHARACTERISTICS:
          (A) LENGTH: 99 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "DNA"

(xi) SEQUENCE DESCRIPTION: SEQ ID NO:2:
```

```
TGTTCTACCA CCTGAACTAG GCTGGCCACA GGAATTATAA AAGCTGAGAA ATTCTTTAAT        60

AATAGTAACC AGGCAACAYC ATTGAAGGCT CATATGTAA                              99
```

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:3:

```
ACAAGATGGT GGACTTGATC CG                                               22
```

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:4:

```
AAGCTTGTTC TACCACCTGA ACTAGGC                                          27
```

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(ix) FEATURE:
        (A) NAME/KEY: mutation
        (B) LOCATION: replace(17, "")
        (D) OTHER INFORMATION: /note= "The nucleic acid at this
            position can be either A or C."

(xi) SEQUENCE DESCRIPTION: SEQ ID NO:5:

```
TTACATATGA GCCTTCNAT                                                   19
```

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:6:

```
TTACATATGA GCCTTCAATG GTGTTGCCT                                        29
```

(2) INFORMATION FOR SEQ ID NO:7:

(i) SEQUENCE CHARACTERISTICS:
        (A) LENGTH: 28 base pairs

```
        (B) TYPE: nucleic acid
        (C) STRANDEDNESS: single
        (D) TOPOLOGY: linear (ii) MOLECULE TYPE: other nucleic acid
         (A) DESCRIPTION: /desc = "DNA"

(xi) SEQUENCE DESCRIPTION: SEQ ID NO:7:

TTACATATGA GCCTTCAATG GTGTTGCC                                        28

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "DNA"

(xi) SEQUENCE DESCRIPTION: SEQ ID NO:8:

TTACATATGA GCCTTCAATG GTGTTGC                                         27

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "DNA"

(xi) SEQUENCE DESCRIPTION: SEQ ID NO:9:

TTACATATGA GCCTTCAATG GTGTTG                                          26

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "DNA"

(xi) SEQUENCE DESCRIPTION: SEQ ID NO:10:

TTACATATGA GCCTTCAATG GTGTT                                           25

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "DNA"

(xi) SEQUENCE DESCRIPTION: SEQ ID NO:11:

TACATATGAG CCTTCAATGG TGT                                             23

(2) INFORMATION FOR SEQ ID NO:12:

(i) SEQUENCE CHARACTERISTICS:
```

(A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:12:

ACATATGAGC CTTCAATGGT G                                              21

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:13:

ATATGAGCCT TCAATGGT                                                  18

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:14:

TTACATATGA GCCTTCAATG G                                              21

(2) INFORMATION FOR SEQ ID NO:15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:15:

TTACATATGA GCCTTCAATG ATGTTGCCT                                      29

(2) INFORMATION FOR SEQ ID NO:16:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:16:

TTACATATGA GCCTTCAATG ATGTTGCC                                       28

(2) INFORMATION FOR SEQ ID NO:17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:17:

TTACATATGA GCCTTCAATG ATGTTGC                                27

(2) INFORMATION FOR SEQ ID NO:18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:18:

TTACATATGA GCCTTCAATG ATGTTG                                 26

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:19:

TTACATATGA GCCTTCAATG ATGTT                                  25

(2) INFORMATION FOR SEQ ID NO:20:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:20:

TACATATGAG CCTTCAATGA TGT                                    23

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:21:

ACATATGAGC CTTCAATGAT G                                      21

(2) INFORMATION FOR SEQ ID NO:22:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:22:

ATATGAGCCT TCAATGAT                                                   18

(2) INFORMATION FOR SEQ ID NO:23:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:23:

TTACATATGA GCCTTCAATG A                                               21

(2) INFORMATION FOR SEQ ID NO:24:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:24:

TGTTCTACCA CCTGAACTAG GC                                              22

(2) INFORMATION FOR SEQ ID NO:25:

(i) SEQUENCE CHARACTERISTICS:
            (A) LENGTH: 240 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:25:

GACTTTGACC GTATATGCTC AGGTGTCCTC CAAGAAATCA AATTTTGCCA CCTCGCCTCA      60

CGAGGCCTGC CCTTCTGATT TTATACCTAA ACAACATGTG CTCCACATTT CAGAACCTAT     120

CTTCTTYGAC ACATGGGATA ACGAGGCTTA TGTGCACGAT GCACCTGTAC GATCACTGAA     180

CTGCACGCTC CGGGACTCAC AGCAAAAAAG CTTGGTGATG TCTGGTCCAT ATGAACTGAA     240

(2) INFORMATION FOR SEQ ID NO:26:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:26:

GAGTCCACAG GAGGTTCTTT AGTTT                                                25

(2) INFORMATION FOR SEQ ID NO:27:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(ix) FEATURE:
        (A) NAME/KEY: mutation
        (B) LOCATION: replace(14, "")
        (D) OTHER INFORMATION: /note= "The nucleic acid at this
            postion can be either A or G."

(xi) SEQUENCE DESCRIPTION: SEQ ID NO:27:

CTCAGGTGTC CTCNAAGAAA TCAAA                                                25

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:28:

GCTTTTTTGC TGTGAGTCCC                                                      20

(2) INFORMATION FOR SEQ ID NO:29:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:29:

AAGCCTCGTT ATCCCATGTG TCGAAGAAG                                            29

(2) INFORMATION FOR SEQ ID NO:30:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:30:

AGCCTCGTTA TCCCATGTGT CGAAGAAG                                             28

(2) INFORMATION FOR SEQ ID NO:31:

(i) SEQUENCE CHARACTERISTICS:
        (A) LENGTH: 27 base pairs

```
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:31:

GCCTCGTTAT CCCATGTGTC GAAGAAG                                          27

(2) INFORMATION FOR SEQ ID NO:32:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:32:

CCTCGTTATC CCATGTGTCG AAGAAG                                           26

(2) INFORMATION FOR SEQ ID NO:33:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:33:

CTCGTTATCC CATGTGTCGA AGAA                                             24

(2) INFORMATION FOR SEQ ID NO:34:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:34:

TCGTTATCCC ATGTGTCGAA GA                                               22

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:35:

CGTTATCCCA TGTGTCGAAG                                                  20

(2) INFORMATION FOR SEQ ID NO:36:

(i) SEQUENCE CHARACTERISTICS:
```

```
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:36:

GTTATCCCAT GTGTCGAA                                                18

(2) INFORMATION FOR SEQ ID NO:37:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:37:

AAGCCTCGTT ATCCCATGTG TCG                                          23

(2) INFORMATION FOR SEQ ID NO:38:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:38:

AAGCCTCGTT ATCCCATGTG TCAAAGAAG                                    29

(2) INFORMATION FOR SEQ ID NO:39:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:39:

AGCCTCGTTA TCCCATGTGT CAAAGAAG                                     28

(2) INFORMATION FOR SEQ ID NO:40:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:40:

GCCTCGTTAT CCCATGTGTC AAAGAAG                                      27

(2) INFORMATION FOR SEQ ID NO:41:
```

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:41:

CCTCGTTATC CCATGTGTCA AAGAAG                                              26

(2) INFORMATION FOR SEQ ID NO:42:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:42:

CTCGTTATCC CATGTGTCAA AGAA                                                24

(2) INFORMATION FOR SEQ ID NO:43:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:43:

TCGTTATCCC ATGTGTCAAA GA                                                  22

(2) INFORMATION FOR SEQ ID NO:44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:44:

CGTTATCCCA TGTGTCAAAG                                                     20

(2) INFORMATION FOR SEQ ID NO:45:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:45:

GTTATCCCAT GTGTCAAA                                                       18

(2) INFORMATION FOR SEQ ID NO:46:

```
    (i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:46:

AAGCCTCGTT ATCCCATGTG TCA                                           23

(2) INFORMATION FOR SEQ ID NO:47:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:47:

AGGTGTCCTC CAAGAAATCA                                               20
```